(12) United States Patent
Matsuyama et al.

(10) Patent No.: US 7,101,670 B2
(45) Date of Patent: Sep. 5, 2006

(54) POLYMORPHIC MARKER THAT CAN BE USED TO ASSESS THE EFFICACY OF INTERFERON THERAPY

(75) Inventors: Noriko Matsuyama, Sagamihara (JP); Masanobu Sugimoto, Kamakura (JP); Michie Hashimoto, Tokyo (JP); Shunji Mishiro, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 542 days.

(21) Appl. No.: 10/270,524

(22) Filed: Oct. 16, 2002

(65) Prior Publication Data

US 2003/0148336 A1    Aug. 7, 2003

(30) Foreign Application Priority Data

Oct. 16, 2001    (JP)  ............................. 2001-318472
May 17, 2002    (JP)  ............................. 2002-143004

(51) Int. Cl.
C12Q 1/68    (2006.01)

(52) U.S. Cl. .......................................................... 435/6

(58) Field of Classification Search ................... None
See application file for complete search history.

(56) References Cited

U.S. PATENT DOCUMENTS 6,667,155 B1    12/2003   Hijikata et al.

FOREIGN PATENT DOCUMENTS

JP           2573443         10/1996

OTHER PUBLICATIONS

Schena et al. Microarrays: biotechnology's discovery platform for functional genomics. Trends in Biotechnology vol. 16:301-306. 1999.*

Schena et al. Trends in Biotechnology vol. 16:301-306. 1999.*

Cividini et al. Journal of Hepatology vol. 27:455-463. 1997.*

J. Muldoon, et al., Genes and Immunity, vol. 2, No. 3, pp. 159-160, XP-001058211, "Novel IFN-α Receptor Promoter Polymorphisms", May 2001.

M. Hijikata, et al., Intervirology, Short Communication, vol. 43, pp. 124-127, "Identification of a Single Nucleotide Polymorphism in the MxA Gene Promoter (G/T at nt-88) Correlated With the Response of Hepatitis C Patients to Interferon", Apr. 17, 2000.

Lutfalla, G. et al. , The Journal of Biological Chemistry, 1992, vol. 267, No. 4, Issue of Feb. 5, pp. 2802-2809, "The Structure of the Human Interferon α/β Receptor Gene".

Muldoon, A., et al., Genes and Immunity, 2001, vol. 2, pp. 159-190, "Novel IFN-α receptor promoter polymorphisms".

Tsubota A. , et al., Hepatology, vol. 19, No. 5, 1994, pp. 1088-1094, "Factors Predictive of Response to Interferon-α Therapy in Hepatitis C Virus Infection".

Matsushita M., et al. Journal of Hepatology, vol. 29, 1998, pp. 695-700, "Association of mannose-binding lectin gene haplotype LXPA and LYPB with interferon-resistant hepatitis C virus infection in Japanese patients".

Chayama K., et al. Journal of Gastroenterology and Hepatology, vol. 8, 1993, pp. 40-44, "Quantitative analysis of hepatitis C virus RNA by competitive nested polymerase chain reaction".

* cited by examiner

*Primary Examiner*—Jeffrey Fredman
*Assistant Examiner*—Heather G. Calamita
(74) *Attorney, Agent, or Firm*—Oblon, Spivak, McClelland, Maier & Neustadt, P.C.

(57) ABSTRACT

The present invention provides a polymorphic marker found in a region of the interferon receptor gene that can be used to assess the efficacy of interferon therapy. Thus, the present invention also relates to methods of assessing the efficacy of interferon therapy in an individual and means for accomplishing such a method.

17 Claims, 6 Drawing Sheets

```
-659  GGGCCCGTGGCTGTTCTCTCCAAGGGACCATCTCGCCCCTCAGCCAAGTCGCCCGGAAAA
-599  CGAGCGCTCGACCGCCTCTGCCCCGCTCTCGGTCTGCACACAGCAACGGTCTGGTCGCTC
-539  AGCCACTTCCTCCTTCCAGCCTCATCTGGTTCCCAGGCCGCTGGGGACTCCCAACGCCAC
-479  TGTCCAAGACTCTAGGGTCAGCAAGCGCCCCGGGCGGAGAAGGGCGAGGACGAAGAGCGC
                ↓ -408
-419  CGGGCCGCGACNAGGAGCCCACCCGCGCCCTCCGACTGCAGACATGGGGAAGAGACGCGG
-359  GGACTCCAAAGTCGCTGGGTCTGCGCAGGTGTGTGCCGCGATCCTGTGAAGGTCAAGGCC
-299  TCCTGTGAGGGGGAGTCGTCCTGGAATGCGATGGTGAAGTGCTCCAGACCGGCCATAGGC
-239  CGGAAAGAGTGAGGAAGAAGAGAATGCAGGAGGCCTGCGATTTCTAAGGCGCGCGCGCAC
-179  AGGGGTGCTGCAATTAGGATGGGGCAATGGGAGCTTGGAGAAGGGGTGCTAGCTAGGAGG
                                              ↓ -77          ↓ -60
-119  AAAGGCGCGTGCGTGGAGGAACGGCGCGTGCGCGGAGGGGCGGTGTGTGTGTGTGTGTGT
                                  ↓ -18         ↓ -3
 -59  CAGAAGAGGCGGCGCGTGCGTAGAGGGGCGGTGAGAGCTAANAGGGGCAGCGCGTGNGCA
   2  GAGGGGCGGTGTGACTTAGGACGGGGCGATGGCGGCTGAGAGGAGCTGCGCGTGCGCGAA
  62  CATGTAACTGGTGGGATCTGCGGCGGCTCCCAGATGATGGTCGTCCTCCTGGGCGCGACG
 122  ACCCTAGTGCTCGTCGCCGTGGCGCCATGGGTGTTGTCCGCAGCCGCAGGTGAGAGGCGG
 182  GGAGGAGAGTCTTGGCGCAGGGCGGGAGGTAGGGCACGCAGCTGGGCTACGGGGCCGGCG
 242  ATGCTGTTGGGGGCGACAGACGCCCAGTCTGGGAAACCTTCGGTCCACTTTGCCGCGCCA
 302  AAGATTAAACCCGACCTGGGCTCGCAAATCAACCAGGAGAAAGTGGTGTTCTGGGTCCTC
 362  TCTTGCCGCTTGCCTGTGCCGTGTACGGTC
```

POLYMORPHIC MARKER THAT CAN BE USED TO ASSESS THE EFFICACY OF INTERFERON THERAPY

FIELD OF THE INVENTION

The present invention relates to a polymorphic marker found in a region of the interferon receptor gene that can be used to assess the efficacy of interferon therapy. Thus, the present invention also relates to methods of assessing the efficacy of interferon therapy in an individual and means for accomplishing such a method.

BACKGROUND OF THE INVENTION

There are about 2,000,000 individuals infected with the hepatitis C virus (hereinafter abbreviated HCV) in Japan. Chronic hepatitis occurs in about 70% of infected individuals, a part of which is considered to lead to the onset of hepatic cancer 10 to 20 years later. Such chronic hepatitis can be treated effectively with interferon (hereinafter abbreviated IFN) α or β. However, the efficacy of IFN α/β has been reported to vary greatly depending on host and viral factors.

Taking into account the substantial side effects associated with IFN treatment, the prolonged treatment period and the high price of the treatment, treating a patient with IFN for whom successful results are not expected creates not only distress for the patient but also a substantial waste of healthcare money paid by the patient or the nation. Accordingly, there is a significant need to develop a method for estimating whether or not successful results can be expected in an individual patient with a particular IFN therapy.

Thus, an object of the invention is to provide a method for estimating whether or not successful results can be expected in an individual patient with a particular IFN therapy.

SUMMARY OF THE INVENTION

Accordingly, one object of the present invention is to provide methods of estimating the efficacy of interferon therapy in an individual to be treated with interferon by determining the genotype of an interferon receptor gene in the individual and based on this genotype, estimating the efficacy of interferon therapy.

In one embodiment of the method, the genotype determined includes determining the number of GT repeats found in the region around −77 in the promoter of the interferon receptor gene; and preferably the individual who would benefit from the interferon therapy would have at least one allele with about 5 GT repeats.

In another embodiment of the method, the interferon receptor gene is interferon α and/or interferon β.

In another embodiment of the method, the individual is infected with a hepatitis C virus.

In another embodiment of the method, the determination of the genotype involves hybridization with specific probes, and in some instances coupled with nucleic acid amplification; amplification can also be used to determine the genotype using specific oligonucleotide primers designed for the detection.

In another embodiment of the method, the determination step is performed at least, in part, on a nucleic acid chip.

Another object of the present invention is to provide an automated process through the use of a computer, computer program, or other data recording and analysis device to estimate the efficacy of interferon therapy in an individual to be treated with interferon.

Another object of the present invention is to provide one or more specific polynucleotide probes and primers that can be used to determine the genotype of an individual for assessing the efficacy of an interferon therapy. In one embodiment of this object, the polynucleotide may be carried or immobilized on a nucleic acid chip, for example, a glass or silicone nucleic acid chip.

BRIEF DESCRIPTION OF THE DRAWINGS

FIG. 1 shows a part of an IFNAR1 gene (SEQ ID NO:4).

DETAILED DESCRIPTION OF THE INVENTION

Figure 2:
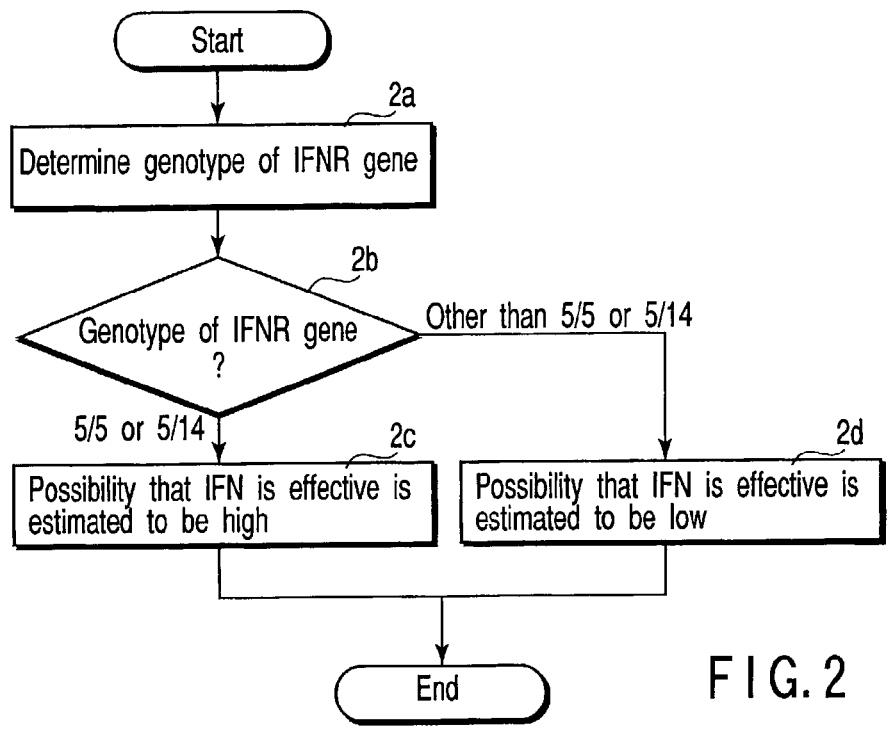
FIG. 2 is a flowchart showing an example of a method according to one aspect of the invention.

The invention is based on our discovery that there is a statistically significant relationship between the genotype of the microsatellite polymorphism of an interferon α receptor type 1 and the efficacy of interferon α and/or β (hereinafter abbreviated IFN α/β).

IFN α and β bind to receptors present on the surface of a cell to transmit a signal, thereby exerting their effects. The gene structure of an interferon α receptor type 1 (hereinafter abbreviated as IFNAR1) which is a receptor for interferons α and β is known (Lufalla, G. et al., J. Biol. Chem. 1992; 267, 2802). A single nucleotide polymorphism (hereinafter abbreviated SNP) and a micropolymorphism consisting of a GT repeat sequence present in a promoter region have been reported (Muldoon, A. et al., Genes and Immunity 2001, 2, 159–169).

The present inventors analyzed the relationship of the SNP and the microsatellite polymorphism present in the promoter region of an IFNAR1 with the efficacy of IFN treatment. As a result, the number of repeats of the GT repeat sequence initiating at about the −77th nucleotide from the transcription initiation point (hereinafter referred to as the −77 position) was found to correlate with the efficacy of interferon therapy.

FIG. 1 shows the region of a IFNAR1 promoter region to the intron 1. The numeral on the left of the sequence represents the position when an mRNA transcription initiation point is regarded to be +1. The SNP's are present in the −408 position, −18 position, and −13 position. The relevant microsatellite polymorphism is present in the region from the −77 position to the −60 position, and the number of repeats of the sequence shown in FIG. 1 is 9. However, this number of repeats varies depending on the genotype of the individual. Accordingly, the position of the microsatellite polymorphism varies depending on the number of repeats. Thus, when the umber of repeats is 5, the position of said microsatellite polymorphism is present in the region from the −69 position to the −60 position, assuming that the transcription initiation point is +1.

The regions other than the polymorphism related with IFN sensitivity and the SNP site having no relation with the IFN sensitivity are common among the sequences shown in FIG. 1. In each sequence shown in the sequence listing and figures in this specification, a "N" or "n", which corresponds to any non-specified base. "N" and "n" represent any of adenine, thymine, guanine and cytosine.

Where the number of repeats of the relevant microsatellite polymorphism in an allele is 5/5 homozygote, or in the case that the number of relevant repeats in any allele is a 5/m heterozygote (wherein "m" is an integer other than 5, preferably 14, including 6, 7, 8, 9, 10, 11, 12, 13, 15, 16, 17, 20, 25, and 26 or more, including all values and subranges there between), the possibility that IFN therapy is effective in an individual to be treated with IFN is high. Conversely, in the case where the number of relevant repeats in any allele is not 5, especially in the case other than a 5/5 homozygote, 5/m heterozygote, or 5/14 heterozygote, the possibility that IFN therapy is effective is low. Thus, according to one aspect of the invention, a GT repeat sequence present in an IFNAR1 gene promoter region is provided as a microsatellite marker for estimating the efficacy of interferon therapy in an individual to be treated with interferon.

The term "high" as it relates to therapy effectiveness as used herein refers to a patient whose blood alanine aminotransferase is within a normal range during a 6-month follow-up period after the IFN therapy and who was negative in the HCV RNA test and can also be characterized as exhibiting complete effectiveness to the therapy. The term "low" as it relates to therapy effectiveness as used herein refers to a patient in which the HCV RNA was found during this same follow-up period or in which the level of alanine aminotransferase was high an can also be characterized as exhibiting non-effectiveness to the therapy.

In this specification, the term "interferon" is used to mean interferon α, β, γ and/or ω. The term "interferon receptor gene" means a gene encoding the receptor for interferon α,β, γ and/or ω, which can be abbreviated IFNR gene. The term "IFNAR1 gene" is a gene encoding the receptor for interferons α and β, especially an interferon α receptor type 1.

"Polymorphic gene" or "polymorphism" employed herein means a group of several alleles occupying a single genetic locus or individual alleles belonging to such an allele group. Among the polymorphism sites, one in which only a single base is different is designated as "single nucleotide polymorphism" or SNP.

"Genotype" means the state of existence of an allele of the relevant genetic locus. "Genotype of an interferon receptor gene" means the number of repeats of the microsatellite polymorphism comprising a GT repeat sequence present in the promoter region of an interferon receptor gene. For convenience, the "genotype" of the microsatellite polymorphism is indicated here as the number of repeats designated by an integer of 1, 2, 3, 4, 5, 6, 7, 8, 9, 10, 11, 12, 13, 14, 15, 16, or more, as well as all values and subranges there between Here "m" is an integer other than 5.

"IFN sensitivity-related polymorphism" means a polymorphic gene which is a determinant of the efficacy of IFN.

"Microsatellite marker" means a GT repeat sequence and is a marker employed as an index allowing the therapeutic effect of IFN to be estimated based on the number of repeats. In particular, a microsatellite marker is a specific site in a specific nucleic acid contained in a sample collected from a subject. Such a marker can be used for estimating the therapeutic effect of IFN.

According to one aspect of the invention, a method for estimating the efficacy of IFN therapy in an individual to be treated with IFN is provided.

According to one aspect of the invention, it is possible to estimate whether or not interferon therapy will be effective in an individual infected with HCV by determining the genotype of the microsatellite polymorphism described above in an individual to be treated with IFN, especially in an individual infected with said HCV, prior to starting IFN therapy. This method can be performed as described herein, for example, including determining the genotype of an IFN receptor gene in the sample obtained from an individual and thenestimating the efficacy of the IFN therapy based on this genotype.

Also according to one aspect of the invention, there is provided a method for estimating the efficacy of IFN therapy in an individual infected with HCV wherein the possibility that the interferon therapy is effective is estimated to be high when in the individual infected with HCV the number of GT repeats in the promoter sequence in the interferon receptor gene in at least one allele is 5, i.e., the genotype the IFN receptor gene is a 5/5 homozygote or 5/m heterozygote (preferably 5/14 heterozygote).

Furthermore, the present invention provides a method for estimating the efficacy of IFN therapy in an individual infected with HCV wherein the possibility that the interferon therapy is effective is estimated to be low when the number of GT repeats described above in any allele in the individual infected with HCV is not 5, i.e., in the case which is neither 5/5 homozygote nor 5/m, for example a 5/14 heterozygote.

Since the indication of IFN therapy is not limited to an individual infected with a hepatitis C virus, one aspect of the invention is a method for estimating the efficacy of interferon therapy in an individual to be treated with IFN by determining the genotype of an IFN receptor gene in a sample obtained from an individual and then estimating the efficacy of the IFN therapy based on the genotype.

An individual who may benefit from the present invention may be a patient with a disease against which IFN therapy is effective, preferably such a disease can be effectively treated with IFN α, β or ω. In one embodiment, the individual may also be a healthy individual. Diseases against which IFN α, β or ω is effective includes, but is not limited to, glioblastoma, medulloblastoma, astrocytoma, dermal malignant melanoma, hepatitis B, stomach cancer, multiple myeloma, hairy cell leukemia, chronic myelocytic leukemia, subacute sclerosing panencephalitis, viral encephalitis, systemic herpes zoster and varicella in immunosuppressed patients, epipharyngeal anaplastic carcinoma, viral internal ear infection accompanied by reduced auditory ability, herpetic keratitis, condyloma latum, condyloma acuminatum, conjunctivitis due to infection with adenovirus and herpes virus, genital herpes, oral herpes, cervical carcinoma, cancerous pleural effusion, keratoacanthoma, basal cell carcinoma, type δ chronic active hepatitis.

Referring to FIG. 2, one aspect of the invention is described. The following procedure is conducted entirely by the operator.

In step 2a, the operator takes a sample such as a blood sample from an individual to be treated with IFN, and initiates an estimation. The sample taken is subjected, if necessary, to a treatment such as purification or extraction and then the genotype of an IFN receptor gene is determined regardless of the order prior to step 2b.

In step 2b, the genotype of the IFN receptor gene determined in step 2a is judged, and the operation jumps to step 2c when the genotype of the relevant microsatellite polymorphism is a 5/5 homozygote or 5/14 heterozygote, while when the genotype of the relevant microsatellite is any other type, the operation jumps to step 2d.

In step 2c, it is estimated, based on the judgment in step 2b, that the possibility that IFN therapy in the relevant individual is effective is high and the entire estimation process is completed.

In step 2d, it is estimated, based on the judgment in step 2b, that the possibility that IFN therapy in the relevant individual is effective is low and the entire estimation process is completed.

Alternatively, to correlate a genotype with IFN sensitivity, for example, Table 1 can be used, for example, for comparison to the genotype of the individual to be screened. From this comparison, the IFN sensitivity of the individual can be assessed.

TABLE 1

| IFNR Genotype | Efficacy |
| --- | --- |
| 5/5 Homozygote | High |
| 5/14 Heterozygote | |
| Others | Low |

The Table can also be in the form of a matrix, chart, graph, and other means of representing correlative data provided that it can be used to correlate genotypes with the effects of IFNs. For example, Table 1 is a table indicating the relationship between the relevant genotype and the effect of an IFN. In the table, the column of "IFNR genotype" indicates the genotype of an interferon receptor gene, while "efficacy" indicates the efficacy of IFN therapy.

The terms "high" and "low" as components described in Table 1 employed here are examples of the designations of the information correlating genotypes with IFN sensitivities or effects of IFNs, and there is no limitation to the letters indicated in this table. Thus, any designation can be employed as long as it can substantially indicate the correlation between a genotype and the effectiveness/non-effectiveness, including "○", "×", "Δ", or numerical values such as scores as simplified values (for example, 1, 2, 3, 4 and 5).

TO determine the genotype of a polymorphism relating to an IFN sensitivity may employ any means known. For example, a nucleic acid containing an intended sequence is prepared from a sample from an individual to be tested, and then the genotype is determined.

An "individual" which is a subject of a method according to one aspect of the invention may be any of mammalian animals including human, dog, cat, cattle, goat, pig, swine, sheep and monkey, preferably the individual is a human.

A "sample" is a biological sample such as blood, serum, lymph, and tissue collected from the individual. The "sample" may also be a sample obtained by subjecting a biological sample to a pretreatment, if necessary, for example, by homogenizing or extracting. Such a pretreatment may be selected appropriately by those skilled in the art depending on the biological sample to be subjected.

A nucleic acid comprising an intended sequence prepared from a biological sample may be prepared from DNA or RNA. For example, providing genomic DNA from a individual may use any means employed ordinarily, including, cellular extraction using, for example, phenol-chloroform, salting out. Additional examples, include with a peripheral blood cell such as a leukocyte, monocyte, lymphocyte and granulocyte by phenol chloroform method, salting out or by using a commercial kit. When mRNA is the sample used for analysis, an oligo-dT column may be employed to selectively enrich for the mRNA.

When the quantity of a polynucleotide is low or insufficient for the assessment, the polynucleotide may be amplified. Such amplification procedures can be accomplished by those methods known in the art, including, for example, the polymerase chain reaction (PCR) and reverse transcription polymerase reaction (RT-PCR).

After performing the extraction and/or amplification procedure, the genotype of an intended polymorphism site can be determined. To determine the genotype any means employed ordinarily can be utilized. For example, those using a direct sequencing method, SSCP method, oligonucleotide hybridization method, specific primer method, and nucleic acid detection chip.

When a nucleotide to be determined is present in a restriction enzyme recognition site, a restriction enzyme fragment-length polymorphism (RFLP) method may also be employed.

Otherwise, a polymorphism can be determined using any known methods including, but not limited to, a PCR-SSP (PCR-specific sequence primers) method, a PCR-SSO (PCR-sequence specific oligonucleotide) method involving a dot blotting method combined with a PCR and a PCR-SSCP method.

The dot blotting method is a method for detecting a nucleic acid sequence contained in a sample using a nucleic acid probe whose sequence is known. In this method, a single-stranded nucleic acid sample is immobilized on an organic substrate and then a solution of a single-stranded probe nucleic acid chain, which can be labeled with, for example, a fluorescent substance, is brought into contact with the sample on this substrate. If the immobilized sequence is complementary to the probe sequence, then they will hybridize to form a double strand, which results in the immobilization of the probe on the substrate. Accordingly, by removing any unreacted probes by washing followed by detecting the label on the probe, the sample nucleic acid chain having the sequence complementary to the probe can be detected. Thus, the present invention also provides probes that can be used in the detecting an IFN sensitivity-related polymorphic gene. Still further, the invention also provides aa reagent or nucleic acid detection chip, containing these probes for estimating whether or not an interferon therapy would be effective in an individual.

Other known factors having effects on the therapeutic performance of IFN α/β on an HCV-infected patient may, for example, be those described below. With regard to viral factors, it is known that the effect of IFN α/β is lower in a patient whose blood virus level is higher and that the therapeutic effect is higher in a patient infected with a type 2 virus rather than one infected with a type 1 virus (A. Tsubota et al., Hepatology 19, 1088–1094, 1994).

It is also known that a patient having the genotype characterized by type XB at the 2 SNPs in a mannose-binding lectin-encoding MBL gene is treated less effectively with IFN α/β compared with a patient having the genotype characterized by type YA (M. Matsushita et al., J. Hepatology 29, 695–700, 1998). On the other hand, it is also known that the SNP present in the MxA gene promoter encoding a MxA protein is related to the interferon therapy sensitivity in a chronic hepatitis C patient (M. Hijikata et al., Intervirology 43, 124–127, 2000). Such an SNP can be determined by amplifying an SNP-containing DNA fragment by a PCR followed by determining its base sequence.

According to the invention, a method for estimating the efficacy of an IFN therapy in an individual to be treated with the IFN by taking the information on the types of these conventional IFN sensitivity-related polymorphic genes and viruses into account in combination with the information on the genotype of a relevant microsatellite polymorphism is provided.

According to one aspect of the invention the analysis described above can be performed with a computer. Thus, the invention also provides a method for estimating the efficacy of an IFN therapy in an individual to be treated with the IFN using a computer. In this method information on the genotype of an IFN receptor gene determined using a sample derived from said individual is inputted into a computer by an operator whereby the the efficacy of the IFN therapybased on the inputted genotype can be estimated by comparing to a chart, table or similar, as described above that correlates the IFN efficacy with a genotype. In a one embodiment, the chart is stored in a storage means in the computer or can be stored on a removable storage media that can be inputted into the computer at the appropriate time. After the correlation, the results of the comparison or assessment can be displayed on the computer on a display device such as, for example, a computer monitor or outputted on for example, a printer.

Figure 3:
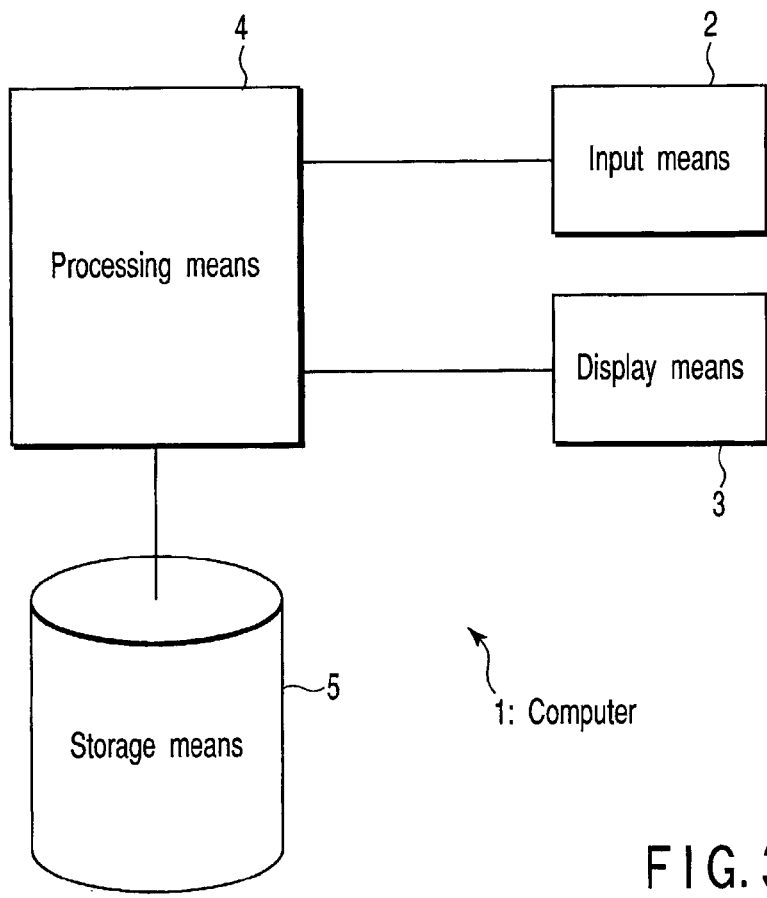
FIG. 3 is a block diagram showing an example of a device to be employed according to one aspect of the invention.
Figure 4:
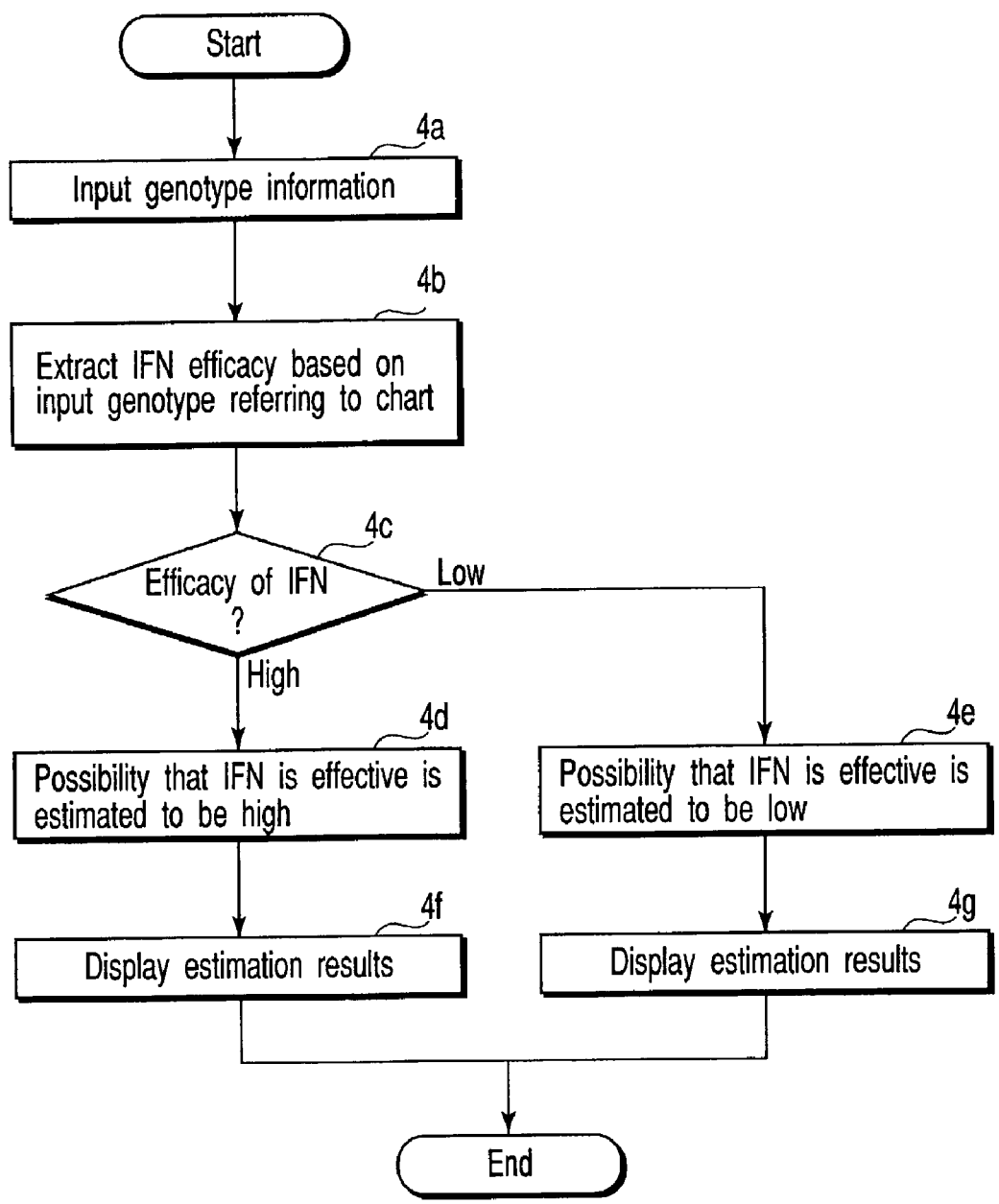
FIG. 4 is a flowchart showing an example of a method according to one aspect of the invention.

FIG. 3 shows a schematic diagram of one aspect of a device for practicing the method of one aspect of the invention. In this figure, a processing means 4 is in communication with a input means 2, a display means 3 and a storage means 5. As shown in FIG. 3, a computer 1 as the aspect is provided at least with the input means 2 with which an operator inputs data to the computer 1, the display means 3 for displaying various information, the processing means 4 for controlling said computer or executing various processing such as a processor or CPU and the storage means 5 for storing programs, charts and the like.

An example of the method using a computer for estimating the efficacy of IFN therapy in an individual to be treated with IFN is described below.

The processing means 4 employed here is a main controlling unit for supervising various parts of the computer, and executes a program stored in a storage unit, which estimates the efficacy of IFN therapy.

In step 4a, when the operator inputs the information on the genotype of an IFN receptor gene via the input means 2, then the information inputted is stored in the storage means 5, and the procedure is jumped to step 4b. The information on the genotype inputted here may be a typical genotype or raw data as long as the information is characteristic of the intended gene.

In step 4b, the processing means 4 reads Chart 1 which correlates a genotype with an IFN efficacy which has previously been stored in the storage means 5 out of stored information and searches the chart whereby abstracting the corresponding IFN efficacy, and the operation is jumped to step 4c.

In step 4c, the processing means 4 judges to forward the operation to step 4d when the IFN efficacy determined in step 4d is "high", or to step 4e when the IFN efficacy determined in step 4d is "low".

In step 4d, the processing means 4 estimates that the possibility that the IFN is effective in the relevant individual is high based on the results obtained in step 4c, and the operation is jumped to step 4f.

In step 4f, the results estimated in step 4d is displayed on the display means 3 and/or stored in the storage means 5 by the processing means 4, whereby completing the entire estimating process. The display accomplished here may be output as an image indicating the efficacy of the IFN therapy which has previously been stored in the storage means 5. If necessary, a loop from step 4f to 4a may be provided.

In step 4e, the processing means 4 estimates that the possibility that the IFN is effective is low based on the results obtained in step 4c, and the operation jumps to step 4g.

In step 4g, the results estimated in step 4e is displayed on the display means 3 and/or recorded in the storage means 5 by the processing means 4, thereby completing the entire estimating process. The display accomplished here may be output as an image indicating the efficacy of the IFN therapy which has previously been stored in the storage means 5. If necessary, a loop from step 4g to 4a may be provided.

While in the method described above the genotype of a microsatellite polymorphism of a relevant IFN receptor gene is determined exclusively and input as information for the estimation, other IFN-sensitivity-related polymorphisms and/or hepatitis C virus type sensitivity markers coupled with the efficacies of IFN therapies, which are known, may also be assessed in combination with the information on the relevant genotype of the IFN gene in the invention and may be inputted as relevant information for the estimation. In such a case, the structure of the chart employed may vary depending on the information to be input.

The methods described herein may be modified without departing from the scope of the invention.

In addition, a computer program for executingthe methods described herein is within the scope of the invention. Such a program is used, for example for the purpose of estimating the efficacy of IFN therapy in an individual to be treated with IFN. This computer program would enable the computer to perform the methods and should include a means for recording information on the genotype of an IFN receptor gene, which is determined from a sample derived from an individual; a means for assessing the efficacy of the IFN therapy, based on the recorded genotype by comparing the genotype to a chart, which correlates the IFN efficacy with the genotype. This chart may be part of the computer program itself or separately stored on the computer or other removable storage media. The computer program should also contain a means for outputting the results of the the comparison.

Furthermore, the computer program described above may enable a computer to function as an inputting means for the genotype information. The computer program itself may be stored on the computer, a removable storage device or any other storage means as is known in the art. A computer device which can perform the herein described methods, preferably with the computer program described above, would include a storage means for storing a chart which correlates a genotype with the efficacy of an IFN; an inputting means for inputting information on the genotype of an IFN receptor gene; an estimating means for estimating the efficacy of the IFN therapy based on the genotype input and a chart stored in said storage means; and da isplay means for displaying the results of the estimation by said estimating means.

From this, therefore, one aspect of the invention is to perform the methods described herein using a computer. Such a method would includerecording information on the genotype of an IFN receptor gene; assessing the efficacy of the IFN therapy, by comparing the recorded genotype to a chart, which correlates IFN efficacy with genotype which has previously been stored in a computer; and outputting the results of the assessment.

Furthermore, to assess the efficacy of IFN therapy can include an inputting step to input information of the genotype of an IFN receptor gene; an estimating step of estimating the efficacy of the IFN therapy based on the inputted genotype and a stored chart, which correlates genotype with the efficacy of an IFN; and a displaying step for displaying the results of the assessment.

One aspect of the invention also provides a polynucleotide for estimating the efficacy of IFN therapy.

In The term "polynucleotide" means a substance formed by binding two or more nucleosides via phosphate bonds. The term "nucleoside" includes, but is not limited to, deoxyribonucleoside and ribonucleoside. Also in the invention, the term "polynucleotide" is intended to include artificially synthesized nucleic acids such as a peptide nucleic acid, morpholino nucleic acid, methylphosphonate nucleic acid, and S-oligo nucleic acid.

The term "promoter region" is intended to mean not only the region which is involved directly in the transcription initiation reaction, such as a TATA box, but also the sequence containing a regulatory sequence which exists proximally or distally to the region described above and which has an influence on the efficiency of the transcription initiation reaction. Accordingly, it should be noted that the term "promoter region" includes either of a sequence involved directly in the transcription initiation reaction or a regulatory sequence and the sequence formed by binding the both.

A polynucleotide may be obtained from a biological sample or be synthesized with a specific desired sequence For preparing a polynucleotide from a biological sample, a sample is taken from an individual, and a polynucleotide is usually extracted from said sample. A method for extracting a polynucleotide from a biological component may, for example, be a phenol extraction, ethanol precipitation or any other extraction methods. When mRNA is extracted, an oligo-dT column can be employed.

A polynucleotide provided according to one aspect of the invention can be employed as a probe or primer for determining the base sequence of a polynucleotide in a sample derived from an individual.

A polynucleotide provided according to one aspect of the invention includes those listed in (a) to (f) described below.

(a) A polynucleotide represented by any one of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12.

(b) A modified polynucleotide formed as a result of the deletion, substitution or addition of one or several nucleotides in a site other than the microsatellite polymorphism site in the promoter region of a polynucleotide listed in (a) described above.

(c) Since among the base sequences of the polynucleotides described above represented by SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11 and SEQ ID NO: 12 one relating to the efficacy of an interferon therapy is a nucleotide present in the microsatellite polymorphism site in the relevant promoter region, a polynucleotide according to one aspect of the invention may be a fragment of the polynucleotide containing said microsatellite polymorphism site. A fragment listed in (c) can preferably be utilized as a probe for the base sequencing of a polynucleotide of a sample derived from an individual. For example, a fragment which is preferable as a probe nucleic acid chain is a base sequence in a promoter region of an IFN receptor gene which is an 8- to 500-nucleic acid chain containing at least an intended microsatellite polymorphism site or a strand complementary thereto. One employed more preferably is one having 10 to 100 nucleotides, a PNA probe of 10 to 15 nucleotides and a DNA probe of 11 to 30 nucleotides especially when used as a probe in a base sequence detection chip. An excessively long polynucleotide fragment poses a difficulty in distinguishing the difference by a single nucleotide. On the other hand, an excessively short polynucleotide on a substrate poses a difficulty in determining the base sequence of a polynucleotide contained in a sample.

Additional polynucleotides than those described herein would include those having at least 75%, 80%, 85%, 90%, 95%, 96%, 97%, 98%, and 99% identity using any known algorithm for assessing percent identity or homology, for example, In addition, those polynucleotides which can be used as probes in the methods described herein would hybridize under stringent conditions to the polynucleotides described herein and the complementary sequences thereof. Stringent conditions can be assessed by the skilled artisan and typically includes a washing step in a hybridization reaction at 65° C. in 0.1×SSC and 0.5% SDS.

SEQ ID NO: 1 is a sequence when the number of the repeats of the relevant microsatellite polymorphism is 5. SEQ ID NO: 2 to SEQ ID NO: 12 are sequences when the numbers of the repeats are 6 to 16, and each is presented as an example whose number of the repeats of the relevant microsatellite polymorphism is other than 5. Accordingly, it is a matter of fact that one whose number of the repeats of the relevant microsatellite polymorphism is 1 to 4 or 16 or more is encompassed in the invention and can preferably be used similarly to the polynucleotides shown here.

(d) The strands complementary to the polynucleotides listed in (a) to (c) shown above may also be employed.

Preferred polynucleotide for use as a probe include those described below.

(e) polynucleotides of SEQ ID NO: 19, SEQ ID NO: 20, SEQ ID NO: 22 and SEQ ID NO: 23;

SEQ ID NO: 19 is a polynucleotide of 30 bases in total length containing a GT repeat sequence with the number of the repeat being 5 at the 3' end thereof;

SEQ ID NO: 20 is a polynucleotide of 32 bases in total length containing a GT repeat sequence with the number of repeats being 6 at the 3' end thereof. The sequence represented by SEQ ID NO: 20 is shown as an example of a polynucleotide containing a GT repeat sequence whose number of repeats is other than 5. Accordingly, a sequence whose number of GT repeats is other than 5 can be employed according to the aspect of the invention similarly to SEQ ID NO: 20, and is preferably a polynucleotide.

SEQ ID NO: 22 is a polynucleotide of 40 bases in total length which has a sequence of a part of a single strand containing a GT repeat microsatellite among the double strand of an IFN receptor gene but does not contain the relevant GT repeat microsatellite in the promoter region and which contains 20 bases from the base adjacent to the 3' end of the relevant GT repeat microsatellite, on the further 3' end of which an AT repeat sequence is present.

SEQ ID NO: 23 is a polynucleotide of 20 bases in total length which has a sequence of a part of a single strand containing a GT repeat microsatellite among the double strand of an IFN receptor gene but does not contain the relevant GT repeat microsatellite in the promoter region and which contains 20 bases from the base adjacent to the 3' end of the relevant GT repeat microsatellite, on the further 3' end of which ferrocene is present.

The sequences in (e) described above are employed preferably by combining each of SEQ ID Nos. 19 and 23 with SEQ ID NO: 22 or 26. For example, one having a predetermined number in the sequence of an intended microsatellite polymorphism site is employed as a probe nucleic acid chain described above whereby examining for any hybridization with a sample, or the difference in the length of the base sequence of a sample hybridized with a probe having an intended microsatellite polymorphism site is detected whereby detecting the number of the repeats of the microsatellite polymorphism site. The difference in the length of the base sequence hybridized with a probe nucleic acid can be detected by measuring the difference in the current derived from the intercalating agent added for example in the case of a current detecting DNA chip. Additional details are described in the examples.

The ferrocene contained in the sequence represented by SEQ ID NO: 23 is a substance added for the purpose of measuring the current. Depending on the detecting means, a label other than ferrocene, such as dye, fluorescent substance, luminescent substance and radioisotope may also be added.

(f) Examples of polynucleotides employed as primers in a PCR reaction are those represented by SEQ ID NO: 13, SEQ ID NO: 14, SEQ ID NO: 15, SEQ ID NO: 16, SEQ ID NO: 17 and SEQ ID NO: 18 as well as those complementary to these polynucleotides.

According to one aspect of the invention, a nucleic acid detection chip provided with a polynucleotide or fragment described hereinis also provided. Such a nucleic acid detection chip is also encompassed in the invention.

Such a chip includes, but is not limited to a fluorescence detection DNA chip, a current detection DNA chip and the like. By estimating the efficacy using a base sequence detection provided with a polynucleotide or a strand complementary thereto as a probe, the estimating method can be simplified and imparted with a higher efficiency. A nucleic acid detection chip can be produced by the procedure described below.

(a) Production of a Fluorescence-detecting Base Sequence Detection Chip

Figures 8, 9:
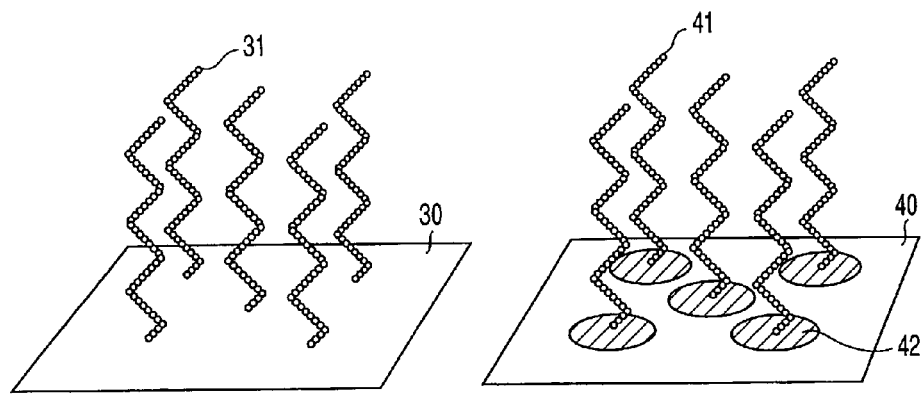
FIG. 8 is a schematic diagram showing an example of a DNA chip according to one aspect of the invention.
FIG. 9 is a schematic diagram showing an example of a DNA chip according to one aspect of the invention.

A polynucleotide, a polynucleotide fragment thereof, or a polynucleotide fragment having a sequence complementary to the sequence thereof may be immobilized as probe 31 on a substrate 30 (see FIG. 8). The substrate may be any substrate employed conventionally such as a glass substrate and a silicone substrate. The immobilization may be performed by means that are known by those skilled in the art, such as employing a spotter, or semiconductor technology.

(b) Production of a Current-detecting Base Sequence Detection Chip

A polynucleotide, a fragment having a part thereof, or a complementary polynucleotide may be immobilized as probe 41 on a substrate 40, for example, a substrate provided with an electrode 42, via a covalent bond, ion bond, physical adsorption or chemical adsorption (see FIG. 9). A current-detecting DNA chip may, for example, bea gene detection device as disclosed in Japanese Patent No. 2573443 registered on Oct. 24, 1996, which is incorporated herein by reference.

In addition to a probe for an IFN receptor gene, a probe for detecting the type of a viral gene and/or a probe for determining the genotype of any other known IFN-sensitivity-related polymorphism can be immobilized together on a single chip. It enables the genotype of an infecting virus and the genotypes of other relevant polymorphisms to be detected simultaneously.

When using a probe capable of detecting a genotype, a plurality of probes corresponding to different genotypes immobilized simultaneously on a substrate may be employed to accomplish highly accurate detection.

In order to detect the genotype of a pathogenic microorganism in a sample, it is also possible to subject a gene of the pathogenic microorganism in the sample to a PCR using primers characteristic to this genotype followed by detection using a chip on which a universal probe is immobilized.

By accomplishing the detection using a probe provided with polynucleotides and a base sequence detection chip according to the aspect of the invention, detection can be simplified and made much more efficient.

The nucleic acid chips described herein may also be utilized with the computer program and/or the computer described herein to perform the methods of the present invention.

EXAMPLES

1. IFNRA1 Gene and Validation of Efficacy of IFN Therapy 1-1. Part 1

Viral types, IFNAR1 gene SNP and microsatellite marker types were determined in individual patientsto investigate the relationship between these indexes and the therapeutic effect.

(1) Outline

DNA and RNA were extracted from blood samples taken from 138 HCV-infected patients and were employed as analytical samples. The RNA fraction was employed to type a virus, and the DNA was employed to analyze the SNP of an IFNAR1 gene and to type a microsatellite marker. Subsequently, the relationship of the therapeutic effect of an IFN α/β with the type of a virus, the SNP of an IFNAR1 gene or microsatellite marker was investigated.

(2) Patients

Samples from 138 HCV-infected patients whose chronic hepatitis C was established based on the blood biochemical, histological and image-analyzing examinations of livers were employed in this investigation. Informed consent was given by all patients with regard to the participation in this investigation. A patient whose blood alanine aminotransferase was within a normal range during the 6-month follow-up period after the IFN α/β therapy and who was negative in the HCV RNA test was judged to exhibit a complete effectiveness. On the other hand, a patient in which the HCV RNA was found during this follow-up period or in which the level of alanine aminotransferase was high was judged to exhibit a non-effectiveness.

(3) HCV, SNP and Microsatellite Typing

39 Samples of the cases exhibiting the interferon therapy efficacy among the hepatitis C patients described above and 99 samples of the cases exhibiting no efficacy (138 samples in total) were analyzed using DNAs extracted from blood or serum. A cDNA was prepared from an RNA extracted from the blood and a part thereof was amplified by PCR, followed by base sequencing and typing of an HCV gene (K.

Chayama et al., J. Gastroenterlo. Hepatol. 8, 40–44, 1993). The SNPs in two positions and the polymorphism of microsatellite in one position (GT: −79–56) of an IFNAR1 promoter were also investigated using the DNA extracted from the blood (Genes and Immunity 2001; 2:159–160).

The sequences employed as the primers were prepared based on the IFNAR sequence of GenBank accession No. X60459, and the transcription initiation site was designated as nt1. With regard to the primers, FNAR1 primer fragments were amplified by GeneAmp PCR 9600 (Roche) using about 1 ng of the DNA together with −629F (5'-TCTCGCCCCT-CAGCCAAGTC-3') and +205R (5'-CAGCTGCGTGC-CCTACCTCC-3') primers.

In the analysis of the SNPs, an amplified fragment. was purified using a MilliPore 96-well clean up filter and subjected to a direct sequencing method using ABI3100 Genetic Analyzer (Applied Biosystems), to determine the base sequence. The number of (GT) repeats was determined by a GeneScan analysis method. Using a PCR fragment obtained from −629F and +205R primers as a template together with 6FAM+92R and −245F primers, one of which was labeled with a fluorescent dye (6-FAM), the PCR was conducted again using ABI3100 Genetic Analyzer GeneScan (ver. 3.7). The PCR employed 30 to 35 cycles of 10 seconds at 95° C., 30 seconds at 58° C. and 30 seconds at 72° C. before and after which the treatments at 95° C. for 2 minutes and at 72° C. for 7 minutes.

(4) Results

138 Patients infected with HCV and having chronic hepatitis were treated with IFN α/β. The relationship between the results and the SNPs is shown in Table 2.

iting complete effectiveness (Table 2). Since the two SNPs (−408C/T and −3C/T) were linked completely and in complete agreement, only one genotype was indicated in Table 2. In a reference reporting the SNP of −408C/T (Genes and Immunity 2001;2: 159–160), the SNP was reported to exist also in the position of −18C/T in western humans. However, in Japanese, there is no SNP in this position and an SNP was newly identified in the position of −3C/T. Accordingly the analysis was conducted as described above.

The relationship of the genotype represented by the GT repeat sequence of a microsatellite with the IFN α/β therapeutic effect is shown in Table 3. While there were 9 genotypes, i.e., 5, 6, 9, and 11 to 16, 5 was predominant. Accordingly, a 5/5 homozygote was present at a higher rate. When comparing all samples regardless of the viral types, the 5/5 homozygote exhibited complete effectiveness in 24 cases (40%) and non-effectiveness in 40 cases (60%), while others exhibited complete effectiveness in 15 cases (20%) and non-effectiveness in 59 cases (80%). These findings reflect a higher efficacy in the 5/5 homozygote population ($p<0.025$). When comparing the 5/5 homozygote or 5-related, i.e., 5/m heterozygote population with the others, the former exhibited complete effectiveness in 39 cases (28%) and non-effectiveness in 85 cases (72%), while the latter exhibited complete effectiveness in 0 cases (0%) and non-effectiveness in 14 cases (100%). These findings reflect a higher efficacy of the IFN α/β in the patients having the genotype 5 or 5 GT repeats on at least one of the alleles in

TABLE 2

Correlation between IFNAR1 promoter site SNPs (−408C/T, −3C/T) and IPN therapy

| IFN Therapy | Number of samples | Viral Type Number of samples | *Genotype | Number of samples | | Allele | |
|---|---|---|---|---|---|---|---|
| Complete effectiveness | 39 | I 12 | C | 9 | (75.0%) | C | 20 (83.3%) |
| | | | C/T | 2 | (16.7%) | T | 4 (16.7%) |
| | | | T | 1 | ( 8.3%) | | |
| | | II 27 | C | 11 | (40.7%) | C | 35 (64.8%) |
| | | | C/T | 13 | (48.2%) | T | 19 (35.2%) |
| | | | T | 3 | (11.1%) | | |
| Non-effectiveness | 99 | I 80 | C | 51 | (63.6%) | C | 128 (80.0%) |
| | | | C/T | 26 | (32.6%) | T | 32 (20.0%) |
| | | | T | 3 | ( 3.8%) | | |
| | | II 19 | C | 13 | (68.4%) | C | 30 (78.9%) |
| | | | C/T | 4 | (21.1%) | T | 8 (21.1%) |
| | | | T | 2 | (10.5%) | | |

*The variation of SNPs (−408C/T, −3C/T) is of an identical base.

Twelve (12) out of 92 patients (13%) infected with the type 1 HCV exhibited complete effectiveness and 80 (87%) exhibited non-effectiveness, while 27 out of 46 patients (57%) infected with the type 2 HCV exhibited complete effectiveness and 19 (43%) exhibited non-effectiveness (Table 2). As also evident from these results, a higher efficacy of treatment with IFN α/β was observed in the patient infected with the type 2 HCV rather than in the patient infected with the type 1 HCV.

T2

Based on the relationship between the 2 SNPs in the IFNAR1 and the therapeutic effect, no particular relationship was noted in the patients infected with type 1 HCV (Table 2). In the patients infected with type 2 HCV, the type T tended to be predominant relatively in the patients exhibthe individual ($p<0.030$). It should be noted that complete effectiveness was not observed in any case where there was no genotype 5 (Table 3).

TABLE 3

Correlation between IFN therapy and number of IFNAR1 (GT) repeats

| | Viral type | | Genotype | | Number of samples |
|---|---|---|---|---|---|
| Complete effectiveness | I | 12 | homo | 7 5/5 | 7 |
| | | | hetero | 5 5/13 | 5 |
| | II | 27 | homo | 17 5/5 | 17 |
| | | | hetero | 10 5/13 | 8 |
| | | | | 5/14 | 2 |

TABLE 3-continued

Correlation between IFN therapy and number of IFNAR1 (GT) repeats

| | Viral type | | Genotype | | | Number of samples |
|---|---|---|---|---|---|---|
| Non-effectiveness | I | 80 | homo | 33 | 5/5 | 33 |
| | | | hetero | 47 | 5/11 | 3 |
| | | | | | 5/12 | 3 |
| | | | | | 5/13 | 15 |
| | | | | | 5/14 | 9 |
| | | | | | 5/15 | 1 |
| | | | | | 5/16 | 2 |
| | | | | | 6/14 | 1 |
| | | | | | 9/13 | 1 |
| | | | | | 11/12 | 1 |
| | | | | | 11/13 | 1 |
| | | | | | 11/14 | 1 |
| | | | | | 12/13 | 5 |
| | | | | | 12/14 | 1 |
| | | | | | 13/14 | 2 |
| | | | | | 13/16 | 1 |
| | II | 19 | homo | 7 | 5/5 | 7 |
| | | | hetero | 12 | 5/12 | 3 |
| | | | | | 5/13 | 5 |
| | | | | | 5/14 | 3 |
| | | | | | 5/15 | |

T3

The results described above indicate a high value of the application based on the ability of avoiding any useless therapy with the IFN α/β, although the number of the target cases was relatively small (14/138=10.1%). It is believed that IFN α exerts its effect by binding to a receptor such as an IFNAR1. Since a microsatellite analyzed here is present in the promoter region involved in the expression of this receptor, it is highly possible that the genotype of this microsatellite may influence the expression of the IFNAR1, which in turn influences the therapeutic effect of IFN α/β.

1-2. Part 2

The samples of 157 cases in total including the new samples from 19 patients and the samples of 138 patients employed in Section 1-1 Part 1 described above were tested similarly to Part 1. That is, viral types, IFNAR1 gene SNP and microsatellite marker types were determined to investigate the relationship of these indexes with the therapeutic effect.

(1) Outline

DNA and RNA were extracted from blood samples taken from 157 HCV-infected patients were employed as analytical samples. The RNA fraction was employed to type a virus, and the DNA was employed to analyze the SNP of an IFNAR1 gene and to type a microsatellite marker. Subsequently, the relationship of the therapeutic effect of an IFN α/β with the type of a virus, the SNP of an IFNAR1 gene or microsatellite marker was investigated.

(2) Patients

Samples from 157 HCV-infected patients whose chronic hepatitis C was established based on the blood biochemical, histological and image-analyzing examinations of livers were employed in this investigation. Informed consent was given by all patients with regard to the participation in this investigation. A patient whose blood alanine aminotransferase was within a normal range during the 6-month follow-up period after the IFN α/β therapy and who was negative in the HCV RNA test was judged to exhibit a complete effectiveness. On the other hand, a patient in which the HCV RNA was found during this follow-up period or in which the level of alanine aminotransferase was high was judged to exhibit a non-effectiveness.

(3) HCV, SNP and Microsatellite Typing

50 Samples of the cases exhibiting efficacy of the interferon therapy among the hepatitis C patients described above and 107 samples of the cases exhibiting no efficacy (157 samples in total) were analyzed using DNAs extracted from blood or serum. A cDNA was prepared from an RNA extracted from the blood and a part thereof was amplified by PCR, followed by a base sequencing and a typing of an HCV gene (K. Chayama et al., J. Gastroenterlo. Hepatol. 8, 40–44, 1993). The SNPs in two positions and the microsatellite polymorphism in one position (GT:79–56) of an IFNAR1 promoter were also investigated using the DNA extracted from the blood (Genes and Immunity 2001; 2:159–160).

The sequences employed as the primers were prepared based on the IFNAR sequence of GenBank accession No. X60459, and the transcription initiation site was designated as nt1. With regard to the primers, FNAR1 primer fragments were amplified by GeneAmp PCR 9600 (Roch) using about 1 ng of the DNA together with −629F and +205R primers.

In the analysis of the SNPs, an amplified fragment was purified using a MilliPore 96-well clean-up filter and subjected to a direct sequencing method using an ABI3100 Genetic Analyzer (Applied Biosystems) todetermine the base sequence. The number of (GT) repeats was determined by a GeneScan analysis method. Using a PCR fragment obtained from −629F and +205R primers as a template together with 6FAM+92R and −245F primers, one of which was labeled with a fluorescent dye (6-FAM), the PCR was conducted again using ABI3100 Genetic Analyzer GeneScan (ver. 3.7). The PCR employed 30 to 35 cycles of 10 seconds at 95° C., 30 seconds at 58° C. and 30 seconds at 72° C. before and after which treatments at 95° C. for 2 minutes and at 72° C. for 7 minutes were provided, respectively.

(4) Results

Figure 7:
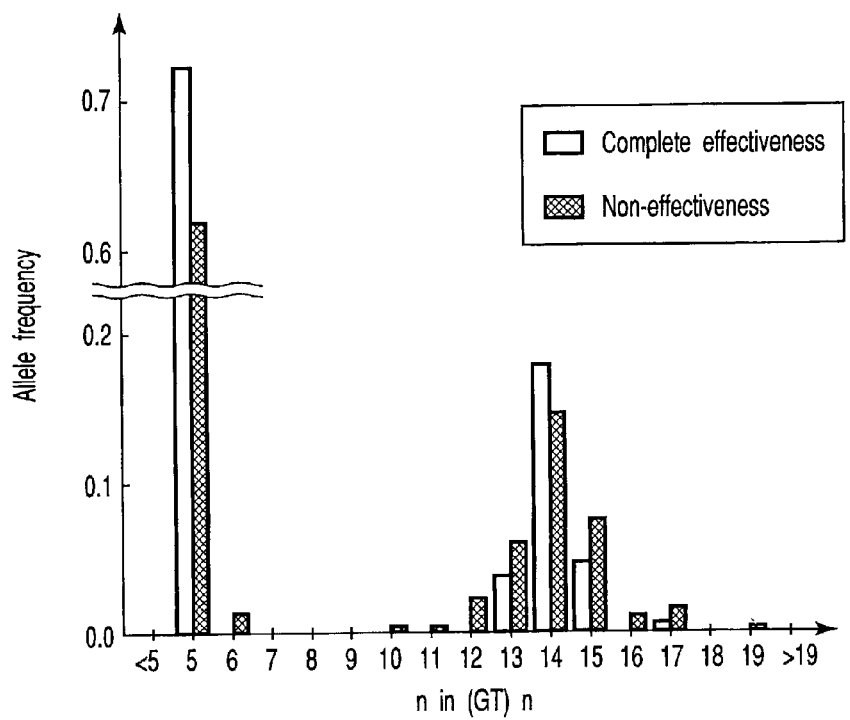
FIG. 7 is a graph showing the frequency of the number of IFNAR1 microsatellite (GTs) observed in a patient treated with interferon exhibiting complete effectiveness and non-effectiveness.

The relationship between the genotype represented by the GT repeat sequence of a microsatellite and the IFN α/β therapeutic effect is shown. There were 11 genotypes, i.e., 5, 6, and 10 to 18. Complete effectiveness was observed at a higher rate than non-effectiveness when the genotype 5 or 14 was possessed, otherwise non-effectiveness was observed at a higher rate than complete effectiveness (FIG. 7).

Based on these findings, the IFN therapy is expected to be effective when the genotype 5 or 14 is possessed, i.e., in the case of a 5/5 homozygote or 5/14 heterozygote. This relationship between the genotype and the IFN α/β therapeutic effect is further detailed in Table 4.

TABLE 4

|  | (GT)n Genotype | | Statistics ($\chi^2$test) |
|---|---|---|---|
| Patient population | 5/5 or 5/14 | Other genotypes | |
| Type 1 HCV-infected patients (n = 102) | | | |
| Complete effectiveness (n = 16) | 13 (81%) | 3 (19%) | P = 0.122* |
| Non-effectiveness (n = 18) | 49 (57%) | 37 (43%) | |
| Type 2 HCV-infected patients (n = 55) | | | |
| Complete effectiveness (n = 34) | 27 (79%) | 7 (21%) | P = 0.462* |
| Non-effectiveness (n = 21) | 14 (67%) | 7 (33%) | |
| Total (n = 157) | | | |
| Complete effectiveness (n = 50) | 40 (80%) | 10 (21%) | P = 0.009* |
| Non-effectiveness (n = 107) | 63 (59%) | 44 (41%) | |

*with Yates' adjustment.

Out of 16 cases exhibiting a complete effectiveness among the patients infected with the type 1 virus, 13 cases (81%) were 5/5 homozygote and 5/14 heterozygote and 3 cases (19%) had other genotypes. Also in the patients infected with the type 2 virus, 27 out of 34 cases (29%) exhibiting complete effectiveness had the 5/5 homozygote and 5/14 heterozygote, and were in a population substantially larger than the population having other genotypes which consisted of 7 cases (21%). On the other hand, in 107 patients exhibiting non-effectiveness, the rates of the patients having the 5/5 homozygote and 5/14 heterozygote and the patients having other genotypes, when combining both viral types, were 59% (63 cases) and 41% (44 cases), respectively. Therefore, the frequency (80%) of the patients having the 5/5 homozygote and 5/14 heterozygote in the patients exhibiting complete effectiveness was statistically significant (p=0.009). These findings indicate that where the genotype is the 5/5 homozygote and 5/14 heterozygote it is highly possible to exhibit complete IFN α/β therapy effectiveness. On the other hand, complete effectiveness was not observed in the patients having no genotype 5 or 14 is noteworthy although the number of the target patients was small (4/157).

2. Repeat Sequence Detection DNA Chip 1

Figure 5:
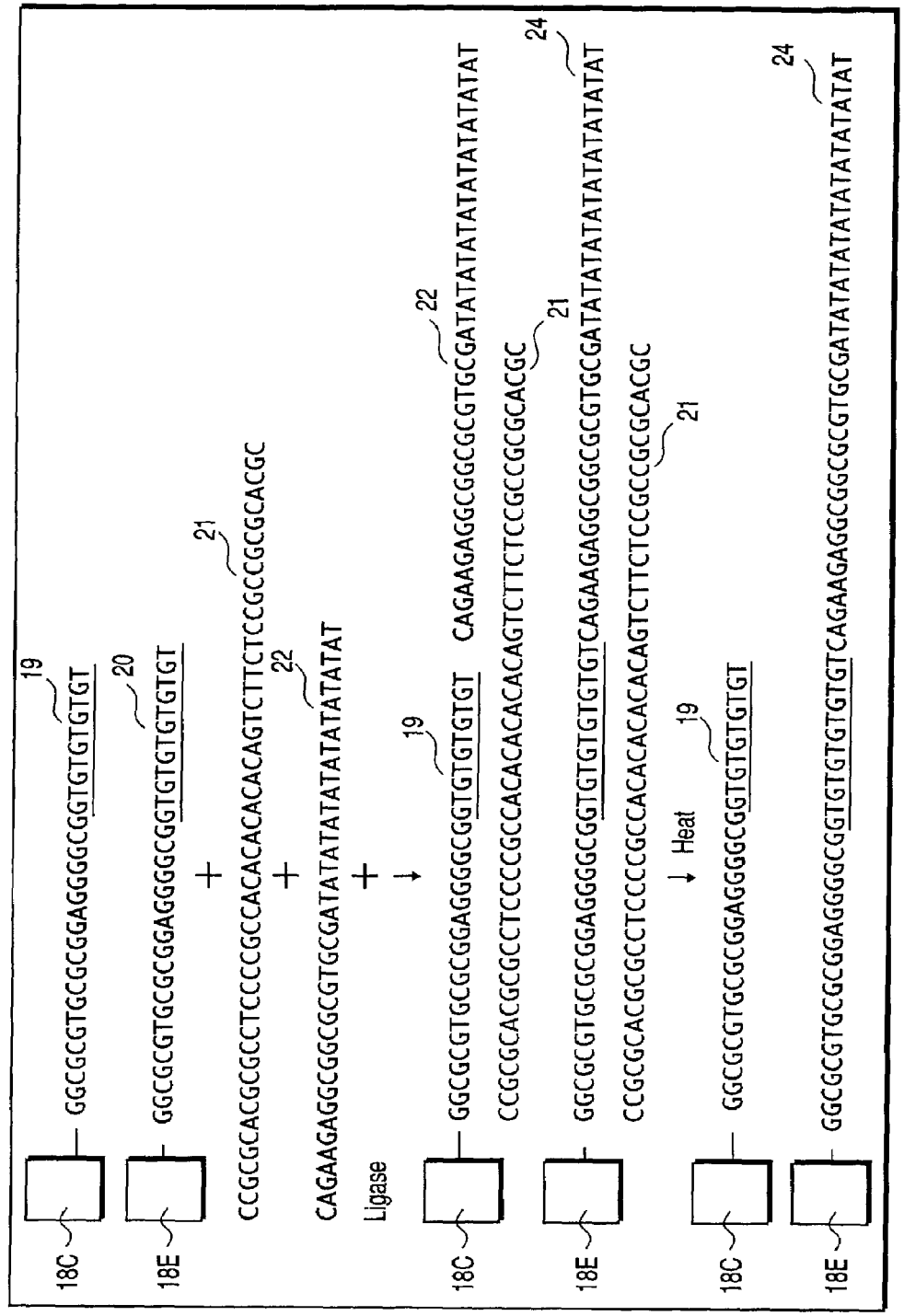
FIG. 5 shows an example of a method according to one aspect of the invention (The sequences are noted by the numbers corresponding to SEQ ID NO: identifiers in the sequence listing).

An example of the repeat sequence detection (or nucleic acid detection chip) using probes containing the polynucleotides represented by SEQ ID NOS: 19, 20 and 22 is discussed with referring to FIG. 5. In this example, a DNA chip on which probe 19 containing the polynucleotide represented by SEQ ID NO: 19 and probe 20 containing the polynucleotide represented by SEQ ID NO: 20 was employed. An example of the detection of the sequence whose number of the repeats was 6 is discussed here. In this example, a current-detecting base sequence detection chip was employed as a DNA chip.

First, electrode 18C (which is fitted with a DNA chip) on which probe 19 whose number of repeats in the GT repeat sequence is 5 and which had a further upstream base sequence and electrode 18E (existing as being fitted with a DNA chip) on which probe 20 having the sequence similar to that of probe 19 except that the number of repeats in the GT repeat sequence are 6 are prepared.

These probes are allowed to hybridize with sample nucleic acid chain 21 containing a target sequence. Subsequently, nucleic acid chain 22 of SEQ ID NO: 22 is reacted. Then a ligase is added to perform a ligation. Then the electrode is heated at 95° C. to denature into a single strand.

In the ligation described above, nucleic acid chain 22 on the surface of the electrode is cleaved because of the absence of the ligation reaction on electrode 18C, while nucleic acid 24 remains in the form of nucleic acid chain 22 bound to probe 19 on electrode 18E. Finally, the increase in the current from electrode 18E is noted when measuring the current from the intercalating agent. Accordingly, the number of the repeats in this sample is revealed to be 6. In a similar manner, the number of the repeats other than 6 can also be identified.

3. Repeat Sequence Detection DNA Chip 2

Figure 6:
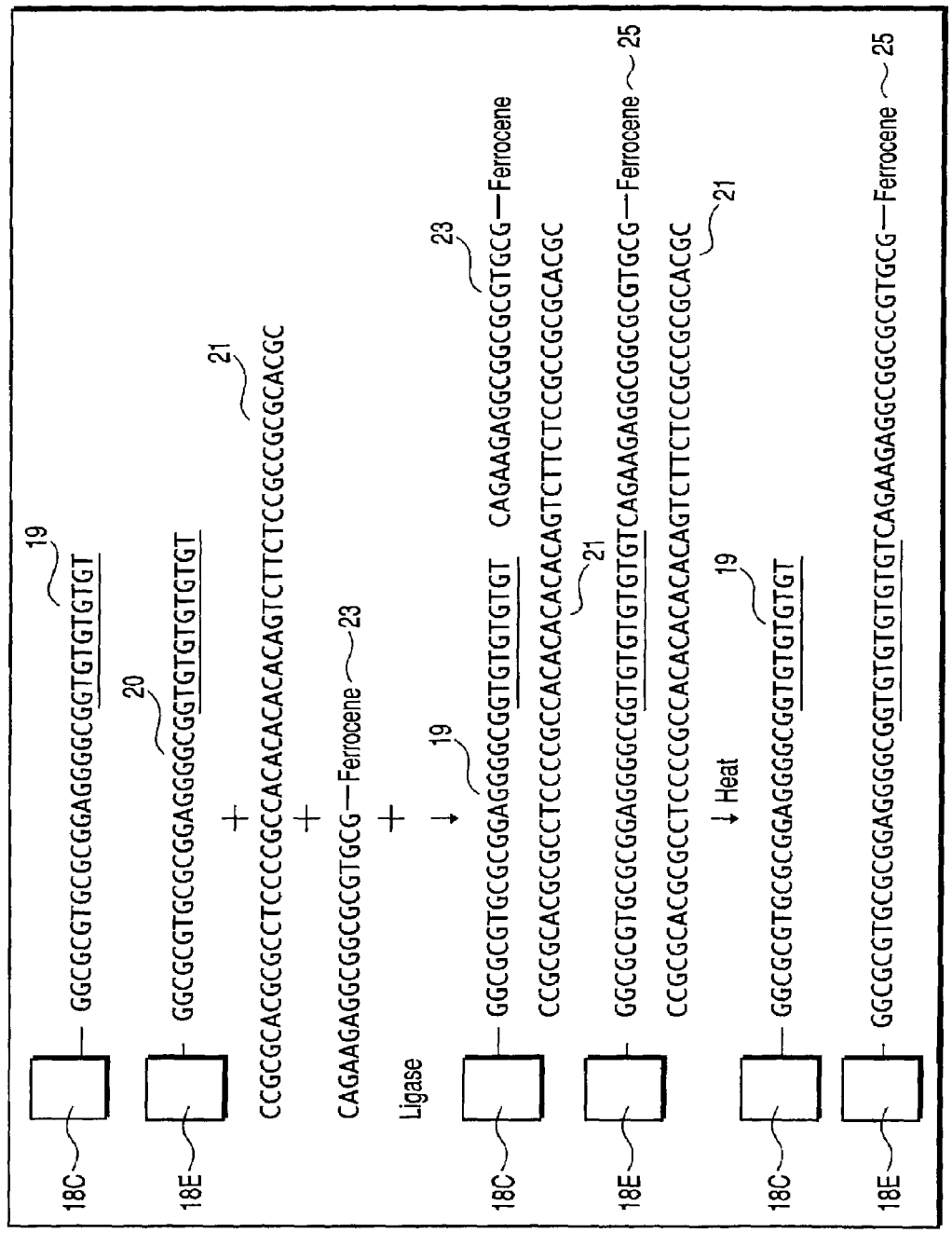
FIG. 6 shows an example of a method according to one aspect of the invention.

An example of the repeat sequence detection (nucleic acid detection chip) using probes containing the polynucleotides represented by SEQ ID NOS: 19, 20 and 23 is discussed with referring to FIG. 6. In this example, a DNA chip on which probe 19 containing the polynucleotide represented by SEQ ID NO:19 and probe 20 containing the polynucleotide represented by SEQ ID NO: 20 was employed. An example of the detection of the sequence whose number of the repeats was 6 is discussed here. In this example, a current-detecting base sequence detection chip was employed as a DNA chip. In this section, an example of the detection of the sequence whose number of the repeats was 6 is discussed.

First, electrode 18C on which probe 19 whose number of repeats is 5 and which electrode 18E on which probe 20 whose number of repeats is 6 are prepared. Then nucleic acid chain 21 containing a target sequence is allowed to hybridize, nucleic acid 23 of SEQ ID NO: 23 labeled with ferrocene is reacted, and a ligase is added to perform a ligation. Then the electrode is heated at 95° C. In this step, the nucleic acid chain on the surface of the electrode 18C is cleaved because of the absence of the ligation reaction on electrode 18C, while nucleic acid 25 remains in the form of nucleic acid chain 23 bound to probe 19 on electrode 18E. Finally, the increase in the current from electrode 18E is noted when measuring the current from ferrocene, thereby verifying that the number of repeats in this sample is 6. In a similar manner, the number of repeats other than 6 can also be identified.

4. Preferred Example of Repeat Sequence Detection DNA Chip and Detection Method Therewith The methods employing the repeat sequence detection DNA chips 1 and 2 described above may be modified as described below.

A DNA chip for detecting the number of repeat sequences in the promoter region of an interferon α receptor gene in a sample may be a DNA chip on which a probe nucleic acid chain which is the nucleic acid chain consisting of a base sequence in the promoter region of said gene which is also a repeat sequence having a certain number of the repeats to be detected and a 5- to 50-base sequence upstream (or downstream) thereof and/or a strand complementary thereto is immobilized. It is preferable to perform each detection using a plural of probe nucleic acid chains which differ in the predetermined number of the repeats described above.

In order to detect the number of the repeat sequences in a sample, a DNA chip described above is used to perform a hybridization of the sample nucleic acid chain. Subsequently, an auxiliary nucleic acid chain for example of 5 to 50 units which is a base sequence in the promoter region in a gene described above and which consists of a base sequence located downstream (or upstream) of the repeat sequence and/or a strand complementary thereto is added, and then a ligase is added for a ligation reaction. In this step, the ligation is advanced and the auxiliary nucleic acid chain is bound downstream (upstream) of the probe nucleic acid chain when the numbers of the repeat sequences of the probe nucleic acid chain and the sample nucleic acid are same, when the ligation is not advanced and the auxiliary nucleic acid chain is not bound to the probe nucleic acid when the numbers of the repeat sequences are different.

As described above, the length of the base sequence of the nucleic acid chain bound finally on the DNA chip varies depending on the number of the repeat sequences in the sample nucleic acid chain. This difference in the length is detected as an electric signal from the probe nucleic acid chain, for example, by adding an intercalating agent which binds specifically to the nucleic acid chain and detecting the current running through the DNA chip, whereby determining whether or not the sample nucleic acid chain has the number of the repeat sequences similar to that of the probe nucleic acid.

When detecting the difference in the base sequence length of a nucleic acid chain bound on a DNA chip based on the difference in the current from the DNA chip, the accuracy can be improved preferably by binding, at a downstream of the auxiliary nucleic acid chain, a substance for promoting the binding of an intercalating agent such as ferrocene or AT repeat sequence.

The present application claims priority to Japanese Patent Application No. 2001-318472 filed on Oct. 16, 2002, the contents of which are incorporated herein by reference.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A method for estimating the efficacy of interferon therapy in an individual to be treated with interferon comprising:

(1) determining the genotype of an interferon receptor gene in a sample from the individual based on the number of GT repeats in a promoter of the interferon receptor gene; and (2) estimating the efficacy of the interferon therapy based on the genotype of the interferon receptor gene, wherein the estimating in (2) comprises indicating the presence of 5GT repeats on at least one allele in the individual is indicative that the interferon therapy will be effective.

2. The method of claim 1, wherein the interferon receptor is an interferon α receptor or an interferon β receptor.

3. The method of claim 1, wherein the individual is infected with a hepatitis C virus.

4. The method of claim 1, wherein the estimating in (2) further comprises indicating that the presence of 5 GT repeats on both alleles in the individual is indicative that the interferon therapy will be effective.

5. The method of claim 1, wherein the estimating in (2) further comprises indicating that the presence of 5 GT repeats on one allele and 14 GT repeats in another allele in the individual is indicative that the interferon therapy will be effective.

6. The method of claim 1, wherein the determining in (1) further comprises amplifying a region of the interferon receptor gene, wherein the region contains a sufficient number of nucleotides to determine the genotype of said interferon receptor gene.

7. A method for estimating the efficacy of interferon therapy in an individual to be treated with interferon comprising:

(1) determining the genotype of an interferon receptor gene in a sample from the individual by hybridizing a sample of genomic DNA obtained from the individual, at least one polynucleotide described in SEQ ID NO: 10, comprising a sequence of a GT repeat in a promoter of the gene and having a length of 11 to 30 nucleotides; and (2) estimating the efficacy of the interferon therapy based on the genotype of the interferon receptor gene.

8. The method of claim 7, wherein the determining in (1) further comprises amplifying a region of the interferon receptor gene, wherein the region contains a sufficient number of nucleotides to determine the genotype of the interferon receptor gene.

9. The method of claim 7, wherein the polynucleotide is a immobilized as a probe on a nucleic acid chip.

10. A method for estimating the efficacy of interferon therapy in an individual to be treated with interferon comprising:

(1) inputting data on a genotype comprising the GT repeats in a promoter region of an interferon receptor gene of the individual into a computer comprising a storage means and a processing means;

(2) abstracting by processing means a degree of the efficacy of the interferon therapy based on the data inputted in (1) from a matrix pre-stored in the storage means of the computer, which correlates the efficacy of interferon therapy with the genotype; and (3) estimating the efficacy of the interferon therapy based on the abstracting in (2) by the processing means, wherein the estimating in (3) comprises indicating that the presence of 5 GT repeats on at least one allele in the individual is indicative that the interferon therapy will be effective.

11. The method of claim 10, wherein the abstracting in (2) by the processing means further comprises outputting the results of the estimating in (2) on a display means.

12. The method of claim 11, wherein the outputting comprises displaying the results of estimating on a computer screen.

13. The method of claim 11, wherein the outputting comprises printing the results of the estimating.

14. The method of claim 10, wherein the interferon receptor is an interferon α or an interferon β receptor.

15. The method of claim 10, wherein the individual is infected with a hepatitis C virus.

16. The method of claim 10, wherein the estimating in (3) further comprises indicating that the presence of 5 GT repeats on both alleles in the individual is indicative that the interferon therapy will be effective.

17. The method of claim 10, wherein the estimating in (3) further comprises indicating that the presence of 5 GT repeats on one allele and 14 GT repeats on another allele in the individual is indicative that the interferon therapy will be effective.

* * * * *

SEQUENCE LISTING

<160> NUMBER OF SEQ ID NOS: 25

<210> SEQ ID NO 1
<211> LENGTH: 1042
<212> TYPE: DNA
<213> ORGANISM: Homo sapiens
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t
<220> FEATURE:
<221> NAME/KEY: misc_feature
<222> LOCATION: (649)..(649)
<223> OTHER INFORMATION: n is a, c, g, or t

<400> SEQUENCE: 1

```
gggcccgtgg ctgttctctc caagggacca tctcgcccct cagccaagtc gcccggaaaa      60
cgagcgctcg accgcctctg ccccgctctc ggtctgcaca cagcaacggt ctggtcgctc     120
agccacttcc tccttccagc ctcatctggt tcccaggccg ctgggactc  ccaacgccac     180 tgtccaagac tctagggtca gcaagcgccc cgggcgaga  aggggcgagga cgaagagcgc     240 cgggccgcga cnaggagccc acccgcgccc tccgactgca gacatgggga agagacgcgg     300
ggactccaaa gtcgctgggt ctgcgcaggt gtgtgccgcg atcctgtgaa ggtcaaggcc     360
tcctgtgagg gggagtcgtc ctggaatgcg atggtgaagt gctccagacc ggccataggc     420
cggaaagagt gaggaagaag agaatgcagg aggcctgcga tttctaaggc gcgcgcgcac     480 agggggtgctg caattaggat gggcaatgg  gagcttggag aagggggtgct agctaggagg     540 aaaggcgcgt gcgtggagga acggcgcgtg cgcggagggg cggtgtgtgt gtcagaagag     600
```

-continued

| | |
|---|---|
| gcggcgcgtg cgtagagggg cggtgagagc taanagggc agcgcgtgng cagaggggcg | 660 |
| gtgtgactta ggacggggcg atggcggctg agaggagctg cgcgtgcgcg aacatgtaac | 720 |
| tggtgggatc tgcggcggct cccagatgat ggtcgtcctc ctgggcgcga cgaccctagt | 780 |
| gctcgtcgcc gtggcgccat gggtgttgtc cgcagccgca ggtgagaggc ggggaggaga | 840 |
| gtcttggcgc agggcgggag gtagggcacg cagctgggct acgggggcgg cgatgctgtt | 900 |
| gggggcgaca gacgcccagt ctgggaaacc ttcggtccac tttgccgcgc caaagattaa | 960 |
| acccgacctg ggctcgcaaa tcaaccagga gaaagtggtg ttctgggtcc tctcttgccg | 1020 |
| cttgcctgtg ccgtgtacgg tc | 1042 |

<210> SEQ ID NO 2
<211> LENGTH: 1044
<212> TYPE: DNA
<213> ORGANISM: Homo sapiens
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (651)..(651)
<223> OTHER INFORMATION: n is a, c, g, or t

<400> SEQUENCE: 2

| | |
|---|---|
| gggcccgtgg ctgttctctc caagggacca tctcgcccct cagccaagtc gcccggaaaa | 60 |
| cgagcgctcg accgcctctg ccccgctctc ggtctgcaca cagcaacggt ctggtcgctc | 120 |
| agccacttcc tccttccagc ctcatctggt tcccaggccg ctggggactc ccaacgccac | 180 |
| tgtccaagac tctagggtca gcaagcgccc cgggcggaga agggcgagga cgaagagcgc | 240 |
| cgggccgcga cnaggagccc accgcgcccc tccgactgca gacatgggga agagacgcgg | 300 |
| ggactccaaa gtcgctgggt ctgcgcaggt gtgtgccgcg atcctgtgaa ggtcaaggcc | 360 |
| tcctgtgagg gggagtcgtc ctggaatgcg atggtgaagt gctccagacc ggccataggc | 420 |
| cggaaagagt gaggaagaag agaatgcagg aggcctgcga tttctaaggc gcgcgcgcac | 480 |
| aggggtgctg caattaggat ggggcaatgg gagcttggag aagggtgct agctaggagg | 540 |
| aaaggcgcgt gcgtggagga acggcgcgtg cgcggagggg cggtgtgtgt gtgtcagaag | 600 |
| aggcggcgcg tgcgtagagg ggcggtgaga gctaanaggg gcagcgcgtg ngcagagggg | 660 |
| cggtgtgact taggacgggg cgatggcggc tgagaggagc tgcgcgtgcg cgaacatgta | 720 |
| actggtggga tctgcggcgg ctcccagatg atggtcgtcc tctgggcgc gacgaccta | 780 |
| gtgctcgtcg ccgtggcgcc atgggtgttg tccgcagccg caggtgagag gcggggagga | 840 |
| gagtcttggc gcagggcggg aggtagggca cgcagctggg ctacggggc ggcgatgctg | 900 |
| ttgggggcga cagacgccca gtctgggaaa ccttcggtcc actttgccgc gccaaagatt | 960 |
| aaacccgacc tgggctcgca aatcaaccag gagaaagtgg tgttctgggt cctctcttgc | 1020 |
| cgcttgcctg tgccgtgtac ggtc | 1044 |

<210> SEQ ID NO 3
<211> LENGTH: 1046
<212> TYPE: DNA
<213> ORGANISM: Homo sapiens
<220> FEATURE:
<221> NAME/KEY: misc_feature

```
<222> LOCATION: (252)..(252)
<223> OTHER INFORMATION: n is a, c, g, or t
<220> FEATURE:
<221> NAME/KEY: misc_feature
<222> LOCATION: (638)..(638)
<223> OTHER INFORMATION: n is a, c, g, or t
<220> FEATURE:
<221> NAME/KEY: misc_feature
<222> LOCATION: (653)..(653)
<223> OTHER INFORMATION: n is a, c, g, or t

<400> SEQUENCE: 3
```

| | | | | | |
|---|---|---|---|---|---|
| gggcccgtgg | ctgttctctc | caagggacca | tctcgcccct | cagccaagtc | gcccggaaaa        60 |
| cgagcgctcg | accgcctctg | ccccgctctc | ggtctgcaca | cagcaacggt | ctggtcgctc       120 |
| agccacttcc | tccttccagc | ctcatctggt | tcccaggccg | ctggggactc | ccaacgccac       180 |
| tgtccaagac | tctagggtca | gcaagcgccc | cgggcggaga | agggcgagga | cgaagagcgc       240 |
| cgggccgcga | cnaggagccc | acccgcgccc | tccgactgca | gacatgggga | agagacgcgg       300 |
| ggactccaaa | gtcgctgggt | ctgcgcaggt | gtgtgccgcg | atcctgtgaa | ggtcaaggcc       360 |
| tcctgtgagg | gggagtcgtc | ctggaatgcg | atggtgaagt | gctccagacc | ggccataggc       420 |
| cggaaagagt | gaggaagaag | agaatgcagg | aggcctgcga | tttctaaggc | gcgcgcgcac       480 |
| agggtgctg  | caattaggat | ggggcaatgg | gagcttggag | aagggtgct  | agctaggagg       540 |
| aaaggcgcgt | gcgtggagga | acggcgcgtg | cgcggagggg | cggtgtgtgt | gtgtgtcaga       600 |
| agaggcggcg | cgtgcgtaga | ggggcggtga | gagctaanag | gggcagcgcg | tgncagagg        660 |
| ggcggtgtga | cttaggacgg | ggcgatggcg | gctgagagga | gctgcgcgtg | cgcgaacatg       720 |
| taactggtgg | gatctgcggc | ggctcccaga | tgatggtcgt | cctcctgggc | gcgacgaccc       780 |
| tagtgctcgt | cgccgtggcg | ccatgggtgt | tgtccgcagc | cgcaggtgag | aggcggggag       840 |
| gagagtcttg | gcgcagggcg | ggaggtaggg | cacgcagctg | ggctacgggg | gcggcgatgc       900 |
| tgttgggggc | gacagacgcc | cagtctggga | aaccttcggt | ccactttgcc | gcgccaaaga       960 |
| ttaaacccga | cctgggctcg | caaatcaacc | aggagaaagt | ggtgttctgg | gtcctctctt      1020 |
| gccgcttgcc | tgtgccgtgt | acggtc |  |  |                 1046 |

```
<210> SEQ ID NO 4
<211> LENGTH: 1048
<212> TYPE: DNA
<213> ORGANISM: Homo sapiens
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (640)..(640)
<223> OTHER INFORMATION: n is a, c, g, or t
<220> FEATURE:
<221> NAME/KEY: misc_feature
<222> LOCATION: (655)..(655)
<223> OTHER INFORMATION: n is a, c, g, or t

<400> SEQUENCE: 4
```

| | | | | | |
|---|---|---|---|---|---|
| gggcccgtgg | ctgttctctc | caagggacca | tctcgcccct | cagccaagtc | gcccggaaaa        60 |
| cgagcgctcg | accgcctctg | ccccgctctc | ggtctgcaca | cagcaacggt | ctggtcgctc       120 |
| agccacttcc | tccttccagc | ctcatctggt | tcccaggccg | ctggggactc | ccaacgccac       180 |
| tgtccaagac | tctagggtca | gcaagcgccc | cgggcggaga | agggcgagga | cgaagagcgc       240 |
| cgggccgcga | cnaggagccc | acccgcgccc | tccgactgca | gacatgggga | agagacgcgg       300 |

```
ggactccaaa gtcgctgggt ctgcgcaggt gtgtgccgcg atcctgtgaa ggtcaaggcc      360
tcctgtgagg gggagtcgtc ctggaatgcg atggtgaagt gctccagacc ggccataggc      420
cggaaagagt gaggaagaag agaatgcagg aggcctgcga tttctaaggc gcgcgcgcac      480
aggggtgctg caattaggat ggggcaatgg gagcttggag aagggtgct agctaggagg       540 aaaggcgcgt gcgtggagga acggcgcgtg cgcggagggg cggtgtgtgt gtgtgtgtca      600
gaagaggcgg cgcgtgcgta gaggggcggt gagagctaan aggggcagcg cgtgngcaga      660
ggggcggtgt gacttaggac ggggcgatgg cggctgagag gagctgcgcg tgcgcgaaca      720
tgtaactggt gggatctgcg gcggctccca gatgatggtc gtcctcctgg gcgcgacgac      780
cctagtgctc gtcgccgtgg cgccatgggt gttgtccgca gccgcaggtg agaggcgggg      840
aggagagtct tggcgcaggg cgggaggtag ggcacgcagc tgggctacgg gggcggcgat      900
gctgttgggg gcgacagacg cccagtctgg gaaaccttcg gtccactttg ccgcgccaaa      960
gattaaaccc gacctgggct cgcaaatcaa ccaggagaaa gtggtgttct gggtcctctc     1020
ttgccgcttg cctgtgccgt gtacggtc                                        1048

<210> SEQ ID NO 5
<211> LENGTH: 1050
<212> TYPE: DNA
<213> ORGANISM: Homo sapiens
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (642)..(642)
<223> OTHER INFORMATION: n is a, c, g, or t
<220> FEATURE:
<221> NAME/KEY: misc_feature
<222> LOCATION: (657)..(657)
<223> OTHER INFORMATION: n is a, c, g, or t

<400> SEQUENCE: 5
gggcccgtgg ctgttctctc caagggacca tctcgcccct cagccaagtc gcccggaaaa       60
cgagcgctcg accgcctctg ccccgctctc ggtctgcaca cagcaacggt ctggtcgctc      120
agccacttcc tccttccagc ctcatctggt tcccaggccg ctggggactc ccaacgccac      180
tgtccaagac tctagggtca gcaagcgccc cgggcggaga agggcgagga cgaagagcgc      240
cgggccgcga cnaggagccc acccgcgccc tccgactgca gacatgggga agagacgcgg      300
ggactccaaa gtcgctgggt ctgcgcaggt gtgtgccgcg atcctgtgaa ggtcaaggcc      360
tcctgtgagg gggagtcgtc ctggaatgcg atggtgaagt gctccagacc ggccataggc      420
cggaaagagt gaggaagaag agaatgcagg aggcctgcga tttctaaggc gcgcgcgcac      480
aggggtgctg caattaggat ggggcaatgg gagcttggag aagggtgct agctaggagg       540 aaaggcgcgt gcgtggagga acggcgcgtg cgcggagggg cggtgtgtgt gtgtgtgtgt      600
cagaagaggc ggcgcgtgcg tagaggggcg gtgagagcta anaggggcag cgcgtgngca      660
gaggggcggt gtgacttagg acggggcgat ggcggctgag aggagctgcg cgtgcgcgaa      720
catgtaactg gtgggatctg cggcggctcc cagatgatgg tcgtcctcct gggcgcgacg      780
accctagtgc tcgtcgccgt ggcgccatgg gtgttgtccg cagccgcagg tgagaggcgg      840
ggaggagagt cttggcgcag ggcgggaggt agggcacgca gctgggctac ggggcggcg       900 atgctgttgg gggcgacaga cgcccagtct gggaaacctt cggtccactt tgccgcgcca      960
aagattaaac ccgacctggg ctcgcaaatc aaccaggaga agtggtgtt ctgggtcctc      1020
```

<210> SEQ ID NO 6
<211> LENGTH: 1052
<212> TYPE: DNA
<213> ORGANISM: Homo sapiens
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (659)..(659)
<223> OTHER INFORMATION: n is a, c, g, or t

<400> SEQUENCE: 6

```
tcttgccgct tgcctgtgcc gtgtacggtc                              1050
gggcccgtgg ctgttctctc caagggacca tctcgcccct cagccaagtc gcccggaaaa   60
cgagcgctcg accgcctctg ccccgctctc ggtctgcaca cagcaacggt ctggtcgctc  120
agccacttcc tccttccagc ctcatctggt tcccaggccg ctggggactc ccaacgccac  180
tgtccaagac tctagggtca gcaagcgccc cgggcggaga agggcgagga cgaagagcgc  240
cgggccgcga cnaggagccc acccgcgccc tccgactgca gacatgggga agagacgcgg  300
ggactccaaa gtcgctgggt ctgcgcaggt gtgtgccgcg atcctgtgaa ggtcaaggcc  360
tcctgtgagg gggagtcgtc ctggaatgcg atggtgaagt gctccagacc ggccataggc  420
cggaaagagt gaggaagaag agaatgcagg aggcctgcga tttctaaggc gcgcgcgcac  480
aggggtgctg caattaggat ggggcaatgg gagcttggag aagggggtgct agctaggagg  540
aaaggcgcgt gcgtggagga acggcgcgtg cgcggagggg cggtgtgtgt gtgtgtgtgt  600
gtcagaagag gcggcgcgtg cgtagagggg cggtgagagc taanaggggc agcgcgtgng  660
cagaggggcg gtgtgactta ggacggggcg atggcggctg agaggagctg cgcgtgcgcg  720
aacatgtaac tggtgggatc tgcggcggct cccagatgat ggtcgtcctc ctgggcgcga  780
cgaccctagt gctcgtcgcc gtggcgccat gggtgttgtc cgcagccgca ggtgagaggc  840
ggggaggaga gtcttggcgc agggcgggag gtagggcacg cagctgggct acggggggcgg  900
cgatgctgtt gggggcgaca gacgcccagt ctgggaaacc ttcggtccac tttgccgcgc  960
caaagattaa acccgacctg ggctcgcaaa tcaaccagga gaaagtggtg ttctgggtcc 1020
tctcttgccg cttgcctgtg ccgtgtacgg tc                              1052
```

<210> SEQ ID NO 7
<211> LENGTH: 1054
<212> TYPE: DNA
<213> ORGANISM: Homo sapiens
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (646)..(646)
<223> OTHER INFORMATION: n is a, c, g, or t
<220> FEATURE:
<221> NAME/KEY: misc_feature
<222> LOCATION: (661)..(661)
<223> OTHER INFORMATION: n is a, c, g, or t

<400> SEQUENCE: 7

-continued

```
gggcccgtgg ctgttctctc caagggacca tctcgcccct cagccaagtc gcccggaaaa       60
cgagcgctcg accgcctctg ccccgctctc ggtctgcaca cagcaacggt ctggtcgctc      120
agccacttcc tccttccagc ctcatctggt tcccaggccg ctggggactc ccaacgccac      180
tgtccaagac tctagggtca gcaagcgccc cgggcggaga agggcgagga cgaagagcgc      240
cgggccgcga cnaggagccc acccgcgccc tccgactgca gacatgggga agagacgcgg      300
ggactccaaa gtcgctgggt ctgcgcaggt gtgtgccgcg atcctgtgaa ggtcaaggcc      360
tcctgtgagg gggagtcgtc ctggaatgcg atggtgaagt gctccagacc ggccataggc      420
cggaaagagt gaggaagaag agaatgcagg aggcctgcga tttctaaggc gcgcgcgcac      480
aggggtgctg caattaggat ggggcaatgg gagcttggag aagggtgct agctaggagg       540 aaaggcgcgt gcgtggagga acggcgcgtg cgcggagggg cggtgtgtgt gtgtgtgtgt      600
gtgtcagaag aggcggcgcg tgcgtagagg ggcggtgaga gctaanaggg gcagcgcgtg      660
ngcagagggg cggtgtgact taggacgggg cgatggcggc tgagaggagc tgcgcgtgcg      720
cgaacatgta actggtggga tctgcggcgg ctcccagatg atggtcgtcc tcctgggcgc      780 gacgaccta gtgctcgtcg ccgtggcgcc atgggtgttg tccgcagccg caggtgagag      840
gcggggagga gagtcttggc gcagggcggg aggtagggca cgcagctggg ctacgggggc      900
ggcgatgctg ttgggggcga cagacgccca gtctgggaaa ccttcggtcc actttgccgc      960
gccaaagatt aaacccgacc tgggctcgca aatcaaccag gagaaagtgg tgttctgggt     1020
cctctcttgc cgcttgcctg tgccgtgtac ggtc                                 1054
```

```
<210> SEQ ID NO 8
<211> LENGTH: 1056
<212> TYPE: DNA
<213> ORGANISM: Homo sapiens
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (648)..(648)
<223> OTHER INFORMATION: n is a, c, g, or t
<220> FEATURE:
<221> NAME/KEY: misc_feature
<222> LOCATION: (663)..(663)
<223> OTHER INFORMATION: n is a, c, g, or t

<400> SEQUENCE: 8
```

```
gggcccgtgg ctgttctctc caagggacca tctcgcccct cagccaagtc gcccggaaaa       60
cgagcgctcg accgcctctg ccccgctctc ggtctgcaca cagcaacggt ctggtcgctc      120
agccacttcc tccttccagc ctcatctggt tcccaggccg ctggggactc ccaacgccac      180
tgtccaagac tctagggtca gcaagcgccc cgggcggaga agggcgagga cgaagagcgc      240
cgggccgcga cnaggagccc acccgcgccc tccgactgca gacatgggga agagacgcgg      300
ggactccaaa gtcgctgggt ctgcgcaggt gtgtgccgcg atcctgtgaa ggtcaaggcc      360
tcctgtgagg gggagtcgtc ctggaatgcg atggtgaagt gctccagacc ggccataggc      420
cggaaagagt gaggaagaag agaatgcagg aggcctgcga tttctaaggc gcgcgcgcac      480
aggggtgctg caattaggat ggggcaatgg gagcttggag aagggtgct agctaggagg       540 aaaggcgcgt gcgtggagga acggcgcgtg cgcggagggg cggtgtgtgt gtgtgtgtgt      600
gtgtgtcaga agaggcggcg cgtgcgtaga ggggcggtga gagctaaanag ggcagcgcg     660 tgngcagagg ggcggtgtga cttaggacgg ggcgatggcg gctgagagga gctgcgcgtg      720
```

```
cgcgaacatg taactggtgg gatctgcggc ggctcccaga tgatggtcgt cctcctgggc    780
gcgacgaccc tagtgctcgt cgccgtggcg ccatgggtgt tgtccgcagc cgcaggtgag    840
aggcggggag gagagtcttg gcgcagggcg ggaggtaggg cacgcagctg ggctacgggg    900
gcggcgatgc tgttggggc gacagacgcc cagtctggga aaccttcggt ccactttgcc    960
gcgccaaaga ttaaacccga cctgggctcg caaatcaacc aggagaaagt ggtgttctgg   1020
gtcctctctt gccgcttgcc tgtgccgtgt acggtc                             1056

<210> SEQ ID NO 9
<211> LENGTH: 1058
<212> TYPE: DNA
<213> ORGANISM: Homo sapiens
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (665)..(665)
<223> OTHER INFORMATION: n is a, c, g, or t

<400> SEQUENCE: 9
gggcccgtgg ctgttctctc aagggacca tctcgcccct cagccaagtc gcccggaaaa     60
cgagcgctcg accgcctctg ccccgctctc ggtctgcaca cagcaacggt ctggtcgctc    120
agccacttcc tccttccagc ctcatctggt tcccaggccg ctggggactc ccaacgccac    180
tgtccaagac tctagggtca gcaagcgccc cgggcggaga agggcgagga cgaagagcgc    240
cgggccgcga cnaggagccc acccgcgccc tccgactgca gacatgggga agagacgcgg    300
ggactccaaa gtcgctgggt ctgcgcaggt gtgtgccgcg atcctgtgaa ggtcaaggcc    360
tcctgtgagg gggagtcgtc ctggaatgcg atggtgaagt gctccagacc ggccataggc    420
cggaaagagt gaggaagaag agaatgcagg aggcctgcga tttctaaggc gcgcgcgcac    480 agggggtgctg caattaggat ggggcaatgg gagcttggag aagggtgct agctaggagg    540 aaaggcgcgt gcgtggagga acggcgcgtg cgcggagggg cggtgtgtgt gtgtgtgtgt    600
gtgtgtgtca gaagaggcgg cgcgtgcgta gagggcggt gagagctaan aggggcagcg    660
cgtgngcaga ggggcggtgt gacttaggac ggggcgatgg cggctgagag gagctgcgcg    720
tgcgcgaaca tgtaactggt gggatctgcg gcggctccca gatgatggtc gtcctcctgg    780
gcgcgacgac cctagtgctc gtcgccgtgg cgccatgggt gttgtccgca gccgcaggtg    840
agaggcgggg aggagagtct tggcgcaggg cgggaggtag ggcacgcagc tgggctacgg    900
gggcggcgat gctgttgggg gcgacagacg cccagtctgg gaaaccttcg gtccactttg    960
ccgcgccaaa gattaaaccc gacctgggct cgcaaatcaa ccaggagaaa gtggtgttct   1020
gggtcctctc ttgccgcttg cctgtgccgt gtacggtc                           1058

<210> SEQ ID NO 10
<211> LENGTH: 1060
<212> TYPE: DNA
<213> ORGANISM: Homo sapiens
<220> FEATURE:
<221> NAME/KEY: misc_feature
<222> LOCATION: (252)..(252)
<223> OTHER INFORMATION: n is a, c, g, or t
<220> FEATURE:
```

<221> NAME/KEY: misc_feature
<222> LOCATION: (652)..(652)
<223> OTHER INFORMATION: n is a, c, g, or t
<220> FEATURE:
<221> NAME/KEY: misc_feature
<222> LOCATION: (667)..(667)
<223> OTHER INFORMATION: n is a, c, g, or t

<400> SEQUENCE: 10

| | | | | | |
|---|---|---|---|---|---|
| gggcccgtgg | ctgttctctc | caagggacca | tctcgcccct | cagccaagtc | gcccggaaaa | 60 |
| cgagcgctcg | accgcctctg | ccccgctctc | ggtctgcaca | cagcaacggt | ctggtcgctc | 120 |
| agccacttcc | tccttccagc | ctcatctggt | tcccaggccg | ctggggactc | ccaacgccac | 180 |
| tgtccaagac | tctagggtca | gcaagcgccc | cgggcggaga | agggcgagga | cgaagagcgc | 240 |
| cgggccgcga | cnaggagccc | acccgcgccc | tccgactgca | gacatgggga | agagacgcgg | 300 |
| ggactccaaa | gtcgctgggt | ctgcgcaggt | gtgtgccgcg | atcctgtgaa | ggtcaaggcc | 360 |
| tcctgtgagg | gggagtcgtc | ctggaatgcg | atggtgaagt | gctccagacc | ggccataggc | 420 |
| cggaaagagt | gaggaagaag | agaatgcagg | aggcctgcga | tttctaaggc | gcgcgcgcac | 480 |
| aggggtgctg | caattaggat | ggggcaatgg | gagcttggag | aagggggtgct | agctaggagg | 540 |
| aaaggcgcgt | gcgtggagga | acggcgcgtg | cgcggagggg | cggtgtgtgt | gtgtgtgtgt | 600 |
| gtgtgtgtgt | cagaagaggc | ggcgcgtgcg | tagaggggcg | gtgagagcta | anaggggcag | 660 |
| cgcgtgngca | gaggggcggt | gtgacttagg | acggggcgat | ggcggctgag | aggagctgcg | 720 |
| cgtgcgcgaa | catgtaactg | gtgggatctg | cggcggctcc | cagatgatgg | tcgtcctcct | 780 |
| gggcgcgacg | accctagtgc | tcgtcgccgt | ggcgccatgg | gtgttgtccg | cagccgcagg | 840 |
| tgagaggcgg | ggaggagagt | cttggcgcag | ggcgggaggt | agggcacgca | gctgggctac | 900 |
| gggggcggcg | atgctgttgg | gggcgacaga | cgcccagtct | gggaaacctt | cggtccactt | 960 |
| tgccgcgcca | aagattaaac | ccgacctggg | ctcgcaaatc | aaccaggaga | aagtggtgtt | 1020 |
| ctgggtcctc | tcttgccgct | tgcctgtgcc | gtgtacggtc | | | 1060 |

<210> SEQ ID NO 11
<211> LENGTH: 1062
<212> TYPE: DNA
<213> ORGANISM: Homo sapiens
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (669)..(669)
<223> OTHER INFORMATION: n is a, c, g, or t

<400> SEQUENCE: 11

| | | | | | |
|---|---|---|---|---|---|
| gggcccgtgg | ctgttctctc | caagggacca | tctcgcccct | cagccaagtc | gcccggaaaa | 60 |
| cgagcgctcg | accgcctctg | ccccgctctc | ggtctgcaca | cagcaacggt | ctggtcgctc | 120 |
| agccacttcc | tccttccagc | ctcatctggt | tcccaggccg | ctggggactc | ccaacgccac | 180 |
| tgtccaagac | tctagggtca | gcaagcgccc | cgggcggaga | agggcgagga | cgaagagcgc | 240 |
| cgggccgcga | cnaggagccc | acccgcgccc | tccgactgca | gacatgggga | agagacgcgg | 300 |
| ggactccaaa | gtcgctgggt | ctgcgcaggt | gtgtgccgcg | atcctgtgaa | ggtcaaggcc | 360 |
| tcctgtgagg | gggagtcgtc | ctggaatgcg | atggtgaagt | gctccagacc | ggccataggc | 420 |

```
cggaaagagt gaggaagaag agaatgcagg aggcctgcga tttctaaggc gcgcgcgcac      480 agggtgctg caattaggat ggggcaatgg gagcttggag aagggtgct agctaggagg        540 aaaggcgcgt gcgtggagga acggcgcgtg cgcggagggg cggtgtgtgt gtgtgtgtgt     600
gtgtgtgtgt gtcagaagag gcggcgcgtg cgtagagggg cggtgagagc taanagggc     660 agcgcgtgng cagaggggcg gtgtgactta ggacggggcg atggcggctg agaggagctg     720
cgcgtgcgcg aacatgtaac tggtgggatc tgcggcggct cccagatgat ggtcgtcctc     780
ctgggcgcga cgaccctagt gctcgtcgcc gtggcgccat gggtgttgtc cgcagccgca    840
ggtgagaggc ggggaggaga gtcttggcgc agggcgggag gtagggcacg cagctgggct    900 acggggggcgg cgatgctgtt gggggcgaca acgcccagt ctgggaaacc ttcggtccac      960
tttgccgcgc caaagattaa acccgacctg ggctcgcaaa tcaaccagga gaaagtggtg    1020
ttctgggtcc tctcttgccg cttgcctgtg ccgtgtacgg tc                       1062
```

<210> SEQ ID NO 12
<211> LENGTH: 1064
<212> TYPE: DNA
<213> ORGANISM: Homo sapiens
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (656)..(656)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t

<400> SEQUENCE: 12

```
gggcccgtgg ctgttctctc caagggacca tctcgcccct cagccaagtc gcccggaaaa      60
cgagcgctcg accgcctctg ccccgctctc ggtctgcaca cagcaacggt ctggtcgctc     120
agccacttcc tccttccagc ctcatctggt tcccaggccg ctggggactc caacgccac     180 tgtccaagac tctagggtca gcaagcgccc cgggcggaga agggcgagga cgaagagcgc    240
cgggccgcga cnaggagccc acccgcgccc tccgactgca gacatgggga agagacgcgg    300
ggactccaaa gtcgctgggt ctgcgcaggt gtgtgccgcg atcctgtgaa ggtcaaggcc    360
tcctgtgagg gggagtcgtc ctggaatgcg atggtgaagt gctccagacc ggccataggc     420
cggaaagagt gaggaagaag agaatgcagg aggcctgcga tttctaaggc gcgcgcgcac    480 agggtgctg caattaggat ggggcaatgg gagcttggag aagggtgct agctaggagg      540 aaaggcgcgt gcgtggagga acggcgcgtg cgcggagggg cggtgtgtgt gtgtgtgtgt    600
gtgtgtgtgt gtgtcagaag aggcggcgcg tgcgtagagg gcggtgaga gctaanaggg   660 gcagcgcgtg ngcagagggg cggtgtgact taggacgggg cgatggcggc tgagaggagc    720
tgcgcgtgcg cgaacatgta actggtggga tctgcggcgg ctcccagatg atggtcgtcc    780
tcctgggcgc gacgacccta gtgctcgtcg ccgtggcgcc atgggtgttg tccgcagccg    840
caggtgagag gcggggagga gagtcttggc gcagggcggg aggtagggca cgcagctggg    900
ctacgggggc ggcgatgctg ttggggggcga cagacgccca gtctgggaaa ccttcggtcc    960
actttgccgc gccaaagatt aaacccgacc tgggctcgca aatcaaccag gagaaagtgg   1020
tgttctgggt cctctcttgc cgcttgcctg tgccgtgtac ggtc                     1064
```

<210> SEQ ID NO 13
<211> LENGTH: 20
<212> TYPE: DNA
<213> ORGANISM: Artificial Sequence
<220> FEATURE:
<223> OTHER INFORMATION: synthetic DNA

<400> SEQUENCE: 13
tctcgcccct cagccaagtc                                               20

<210> SEQ ID NO 14
<211> LENGTH: 20
<212> TYPE: DNA
<213> ORGANISM: Artificial Sequence
<220> FEATURE:
<223> OTHER INFORMATION: synthetic DNA

<400> SEQUENCE: 14
cagctgcgtg ccctacctcc                                               20

<210> SEQ ID NO 15
<211> LENGTH: 20
<212> TYPE: DNA
<213> ORGANISM: Artificial Sequence
<220> FEATURE:
<223> OTHER INFORMATION: synthetic DNA

<400> SEQUENCE: 15
gactctaggg tcagcaagcg                                               20

<210> SEQ ID NO 16
<211> LENGTH: 20
<212> TYPE: DNA
<213> ORGANISM: Artificial Sequence
<220> FEATURE:
<223> OTHER INFORMATION: synthetic DNA

<400> SEQUENCE: 16
cagctgcgtg ccctacctcc                                               20

<210> SEQ ID NO 17
<211> LENGTH: 20
<212> TYPE: DNA
<213> ORGANISM: Artificial Sequence
<220> FEATURE:
<223> OTHER INFORMATION: synthetic DNA

<400> SEQUENCE: 17
taggccggaa agagtgagga                                               20

<210> SEQ ID NO 18
<211> LENGTH: 20
<212> TYPE: DNA
<213> ORGANISM: Artificial Sequence
<220> FEATURE:
<223> OTHER INFORMATION: synthetic DNA

<400> SEQUENCE: 18
aggaggacga ccatcatctg                                               20

<210> SEQ ID NO 19
<211> LENGTH: 30
<212> TYPE: DNA
<213> ORGANISM: Artificial Sequence
<220> FEATURE:
<223> OTHER INFORMATION: synthetic DNA

```
<400> SEQUENCE: 19
ggcgcgtgcg cggaggggcg gtgtgtgtgt                              30

<210> SEQ ID NO 20
<211> LENGTH: 32
<212> TYPE: DNA
<213> ORGANISM: Homo sapiens

<400> SEQUENCE: 20
ggcgcgtgcg cggaggggcg gtgtgtgtgt gt                           32

<210> SEQ ID NO 21
<211> LENGTH: 52
<212> TYPE: DNA
<213> ORGANISM: Homo sapiens

<400> SEQUENCE: 21
ccgcgcacgc gcctccccgc cacacacaca cagtcttctc cgccgcgcac gc     52

<210> SEQ ID NO 22
<211> LENGTH: 40
<212> TYPE: DNA
<213> ORGANISM: Artificial Sequence
<220> FEATURE:
<223> OTHER INFORMATION: synthetic DNA

<400> SEQUENCE: 22
cagaagaggc ggcgcgtgcg atatatatat atatatatat                   40

<210> SEQ ID NO 23
<211> LENGTH: 20
<212> TYPE: DNA
<213> ORGANISM: Homo sapiens

<400> SEQUENCE: 23
cagaagaggc ggcgcgtgcg                                         20

<210> SEQ ID NO 24
<211> LENGTH: 72
<212> TYPE: DNA
<213> ORGANISM: Artificial Sequence
<220> FEATURE:
<223> OTHER INFORMATION: synthetic DNA

<400> SEQUENCE: 24
ggcgcgtgcg cggaggggcg gtgtgtgtgt gtcagaagag gcggcgcgtg cgatatatat    60
atatatatat at                                                 72

<210> SEQ ID NO 25
<211> LENGTH: 52
<212> TYPE: DNA
<213> ORGANISM: Artificial Sequence
<220> FEATURE:
<223> OTHER INFORMATION: synthetic DNA

<400> SEQUENCE: 25
ggcgcgtgcg cggaggggcg gtgtgtgtgt gtcagaagag gcggcgcgtg cg     52
```